US009102754B2

(12) United States Patent
Napper et al.

(10) Patent No.: US 9,102,754 B2
(45) Date of Patent: Aug. 11, 2015

(54) IMMUNOMODULATORY COMPOSITIONS AND METHODS FOR TREATING DISEASE WITH MODIFIED HOST DEFENSE PEPTIDES

(75) Inventors: Scott Kirk Napper, Saskatoon (CA); Kenneth Jason Kindrachuk, Vancouver (CA); Samuel Kwadwo Attah-Poku, Saskatoon (CA)

(73) Assignee: University of Saskatchewan (CA)

( * ) Notice: Subject to any disclaimer, the term of this patent is extended or adjusted under 35 U.S.C. 154(b) by 921 days.

(21) Appl. No.: 12/666,229

(22) PCT Filed: Jun. 27, 2008

(86) PCT No.: PCT/CA2008/001221
§ 371 (c)(1),
(2), (4) Date: May 11, 2010

(87) PCT Pub. No.: WO2009/000089
PCT Pub. Date: Dec. 31, 2008

(65) Prior Publication Data
US 2010/0221272 A1 Sep. 2, 2010

Related U.S. Application Data

(60) Provisional application No. 60/946,888, filed on Jun. 28, 2007, provisional application No. 60/989,392, filed on Nov. 20, 2007.

(51) Int. Cl.
*A61K 38/14* (2006.01)
*A61K 38/16* (2006.01)
*C07K 14/47* (2006.01)
*A61K 39/39* (2006.01)
*A61K 38/00* (2006.01)
*A61K 39/00* (2006.01)

(52) U.S. Cl.
CPC ............. *C07K 14/4723* (2013.01); *A61K 39/39* (2013.01); *A61K 38/00* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 3,817,837 | A | 6/1974 | Rubenstein |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,391,904 | A | 7/1983 | Litman et al. |
| 5,212,204 | A * | 5/1993 | Keefer et al. ............... 514/647 |

FOREIGN PATENT DOCUMENTS

| | | |
|---|---|---|
| WO | WO 2005/007758 A2 | 1/2005 |
| WO | WO 2007/064903 * | 6/2007 |

OTHER PUBLICATIONS

Nagpal et al, Plasticity in structure and interactions is critical for the action of indolicidin, an antibacterial peptide of innate immune origin, Protein Science (2002), 11:2158-2167.*
Napgal et al, Plasticity in structure and interactions is critical for the action of indolicidin, an antibacterial peptide of innate immune, origin, Protein Science (2002), 11:2158-2167.*
Guichard et al, Antigenic mimicry of natural L-peptides with retro-inversopeptidomimetics, Proc. Nati. Acad. Sci. vol. 91, pp. 9765-9769, Oct. 1994.*
Risso et al, BMAP-28, an Antibiotic Peptide of Innate Immunity, Induces Cell Death through Opening of the Mitochondrial Permeability Transition Pore, Molecular and Cellular Biology, Mar. 2002, vol. 22, No. 6, p. 1926-1935.*
Steinstraesser, Sepsis—New strategies with host defense peptides?, Crit Care Med 2004 vol. 32, No. 12, pp. 2555-6.*
Oren et al, Selective Lysis of Bacteria but Not Mammalian Cells by Diastereomers of Melittin: Structure-Function Study, Biochemistry 1997, 36, 1826-1835.*
Oren et al, A Repertoire of Novel Antibacterial Diastereomeric Peptides with Selective Cytolytic Activity, The Journal of Biological Chemistry vol. 272, No. 23, Issue of Jun. 6, pp. 14643-14649, 1997.*
Skerlavaj et al, Biological Characterization of Two Novel Cathelicidin-derived Peptides and Identification of Structural Requirements for Their Antimicrobial and Cell Lytic Activities, The Journal of Biological Chemistry vol. 271, No. 45, Issue of Nov. 8, pp. 28375-28381, 1996.*
Al-Obeidi, F. et al., "Peptide and Peptidomimetic Libraries," Molecular Biotechnology,1998, pp. 205-223, vol. 9.
Altschul, S.F. et al., "Basic Local Alignment Search Tool," J. Mol. Biol., 1990, pp. 403-410, vol. 215.
Altschul, S.F. et al., "Gapped BLAST and PSI-BLAST: A New Generation of Protein Database Search Programs," Nucleic Acids Research, 1997, pp. 3389-3402, vol. 25, No. 17.

(Continued)

*Primary Examiner* — Karlheinz R Skowronek
*Assistant Examiner* — Sergio Coffa
(74) *Attorney, Agent, or Firm* — Kilpatrick Townsend & Stockton LLP

(57) ABSTRACT

Compositions and methods are provided for modulating an immune response in a vertebrate subject. Compositions and methods can comprise administering a modified host defense peptide to the vertebrate subject in an amount effective to activate the immune response in the vertebrate subject, wherein the modified host defense peptide is inverted in amino acid sequence from an amino terminus to a carboxy terminus or modified to one or more D-amino acids, or both modifications, when compared to a host defense peptide. Compositions and methods are provided which comprise administering a modified host defense peptide to the vertebrate subject in an amount effective to modify an immune response in the vertebrate subject.

28 Claims, 9 Drawing Sheets

(56) References Cited

OTHER PUBLICATIONS

Angus, D.C. et al., "Epidemiology of Sever Sepsis in the United States: Analysis of Incidence, Outcome, and Associated Costs of Care," Crit, Care Med, 2001, pp. 1303-1310, vol. 29, No. 7.

Bader, M.W. et al., "Recognition of Antimicrobial Peptides by a Bacterial Sensor Kinase," Cell, 2005, pp. 461-472, vol. 122.

Belousov, E.S. et al., "Sequence-Specific Targeting and Covalent Modification of Human Genomic DNA," Nucleic Acids Research, 1997, pp. 3440-3444, vol. 25, No. 17.

Benincasa, M. et al., "In Vitro and in Vivo Antimicrobial Activity of Two α-Helical Cathelicidin Peptides and of Their Synthetic Analogs," Peptides, 2003, pp. 1723-1731, vol. 24.

Benincasa, M. et al., "Fungicidal Activity of Five Cathelicidin Peptides Against Clinically Isolated Yeasts," Journal of Antimicrobial Chemotherapy, Oct. 5, 2006, pp. 950-959, vol. 58.

Berge, S.M. et al., "Pharmaceutical Salts", Journal of Pharmaceutical Sciences, Jan. 1977, pp. 1-19, vol. 66, No. 1.

Blommers, M.J.J. et al., "Effects of the Introduction of L-Nucleotides into DNA. Solution Structure of the Heterochiral Duplex d(G-C-G-(L)T-G-C-G)d(C-G-C-A-C-G-C) Studied by NMR Spectroscopy," Biochemistry, 1994, pp. 7886-7896, vol. 33.

Bommineni, Y.R. et al., "Fowlicidin-3 is an α-Helical Cationic Host Defense Peptide with Potent Antibacterial and Lipopolysaccharide-Neutralizing Activities," FEBS Journal, 2007, pp. 418-428, vol. 274.

Bowdish, D.M.E. et al., "A Re-Evaluation of the Role of Host Defence Peptides in Mammalian Immunity," Current Protein and Peptide Science, 2005, pp. 1-17, vol. 6.

Bowdish, D.M.E. et al., "Immunomodulatory Activities of Small Host Defense Peptides," Antimicrobial Agents and Chemotherapy, 2005, pp. 1727-1732, vol. 493.

Bowdish, D.M.E. et al., "Impact of LL-37 on Anti-Infective Immunity," Journal of Leukocyte Biology, Apr. 2005, pp. 451-459, vol. 77.

Bowdish, D.M.E. et al., "The Human Cationic Peptide LL-37 Induces Activation of the Extracellular Signal-Regulated Kinase and p38 Kinase Pathways in Primary Human Monocytes," Journal of Immunology, 2004, pp. 3758-3765, vol. 172.

Braff, M.H. et al., "Structure-Function Relationships Among Human Cathelicidin Peptides: Dissociation of Antimicrobial Properties from Host Immunostimulatory Activities," J. Immunol., 2005, pp. 4271-4278, vol. 174, No. 7.

Brickman, E. et al., "Analysis of the Regulation of Escherichia coli Alkaline Phosphatase Synthesis Using Deletions and ø80 Transducing Phages," J. Mol. Biol. 96: 307-316, 1975.

Brötz, H. et al., "The Lantibiotic Mersacidin Inhibits Peptidoglycan Synthesis by Targeting Lipid II," Antimicrobial Agents and Chemotherapy, Jan. 1998, pp. 154-160, vol. 42, No. 1.

Caruthers, M.H. et al., "New Chemical Methods for Synthesizing Polynucleotides," Nucleic Acids Research, Symposium Series No. 7, 1980, pp. 215-223.

Cevc, G. et al., "Ultraflexible Vesicles, Transfersomes, Have an Extremely Low Pore Penetration Resistance and Transport Therapeutic Amounts of Insulin Across the Intact Mammalian Skin," Biochimica et Biophysica Acta, 1998, pp. 201-215, vol. 1368.

Chen, Y. et al., "Rational Design of α-Helical Antimicrobial Peptides with Enhanced Activities and Specificity/Therapeutic Index," J. Biol. Chem., Apr. 1, 2005, pp. 12316-12329, vol. 28, No. 13.

Chen, Y. et al., "Comparison of Biophysical and Biologic Properties of α-Helical Enantiomeric Antimicrobial Peptides," Chem. Biol. Drug Des., 2006, pp. 162-173, vol. 67.

Cho, U.S. et al., "Metal Bridges Between the PhoQ Sensor Domain and the Membrane Regulate Transmembrane Signaling," J. Mol. Biol., 2006, pp. 1193-1206, vol. 356.

Chorev, M. et al., "Recent Developments in Retro Peptides and Proteins—an Ongoing Topochemical Exploration," TIBTECh, Oct. 1995, pp. 438-445, vol. 13.

Cirioni, O. et al., "LL-37 Protects Rats Against Lethal Sepsis Caused by Gram-Negative Bacteria," Antimicrobial Agents and Chemotherapy, May 2006, pp. 1672-1679, vol. 50, No. 5.

Clapp, W.D. et al., "Grain Dust-Induced Airflow Obstruction and Inflammation of the Lower Respiratory Tract," Am. J. Respir. Cri. Care Med., 1994, pp. 611-617, vol. 150.

Cole, A.M. et al., "Inhibition of Neutrophil Elastase Prevents Cathelicidin Activation and Impairs Clearance of Bacteria from Wounds," Blood, 2001, pp. 297-304, vol. 97.

Dhople, V et al., "The Human Beta-Defensin-3, an Antibacterial Peptide with Multiple Biological Functions," Biochimica et Biophysica Acta, 2006, pp. 1499-1512, vol. 1758.

Dobeli, H. et al., "Recombinant Fusion Proteins for the Industrial Production of Disulfide Bridge Containing Peptides: Purification, Oxidation without Concatamer Formation, and Selective Cleavage," Protein Expressions and Purification, 1998, pp. 404-414, vol. 12.

Donnarumma, G et al., "Anti-Inflammatory Effects of Moxifloxacin and Human β-Defensin 2 Association in Human Lung Epithelial Cell Line (A549) Stimulated with Lipopolysaccharide," Peptides, 2007, pp. 2286-2292, vol. 28.

Elahi, S. et al., "The Host Defense Peptide Beta-Defensin 1 Confers Protection Against Bordetella pertussis in Newborn Piglets," Infection and Immunity, Apr. 2006, pp. 2338-2352, vol. 74, No. 4.

Elssner, A. et al., "A Novel P2X7 Receptor Activator, the Human Cathelicidin-Derived Peptide LL37, Induces IL-1 β Processing and Release," J. Immunol., 2004, pp. 4987-4994, vol. 172.

Fauchere, J-L. et al., "Evaluation of the Stability of Peptides and Pseudopeptides as a Tool in Peptide Drug Design," Advances in Drug Research, 1992, pp. 127-159, vol. 23.

Fernandez, M.L. et al., "Bacteremic Pneumococcal Infections in Immunocompromised Patients Without AIDS: the Impact of β-Lactam Resistance on Mortality," Int. J. Infect. Dis., 2003, pp. 46-52, vol. 7.

Finking, R. et al., "Biosynthesis of Nonribosomal Peptides," Annu. Rev. Microbiol., 2004, pp. 453-488, vol. 58.

Finlay, B.B. et al., "Can Innate Immunity be Enhanced to Treat Microbial Infections," Nature Reviews Microbiology, Jun. 2004, pp. 497-504, vol. 2.

Fischer, P.M., "The Design, Synthesis and Application of Stereochemical and Directional Peptide Isomers: A Critical Review," Curreng Protein and Peptide Science, 2003, pp. 339-356, vol. 4.

Frenkel, K. et al., "7,12-Dimethylbenz[a]Anthracene Induces Oxidative DNA Modification in Vivo," Free Radical Biology & Medicine, 1995, pp. 373-380, vol. 19, No. 3.

Fukumoto, K. et al., "Effect of Antibacterial Cathelicidin Peptide CAP18/LL-37 on Sepsis in Neonatal Rats," Pediatr. Surg. Int., 2005, pp. 20-24, vol. 21.

Gallo, R.L. et al., "Biology and Clinical Relevance of Naturally Occurring Antimicrobial Peptides," J. Allergy Clin. Immunol., Dec. 2002, pp. 823-831, vol. 10.

Ganz, T. et al., "Microbicidal/Cytotoxic Proteins of Neutrophils are Deficient in Two Disorders: Chediak-Higashi Syndrome and "Specific" Granule Deficiency," J. Clin. Invest., Aug. 1988, pp. 552-556, vol. 82.

Ghiselli, R et al., "Effects of the Antimicrobial Peptide BMAP-27 in a Mouse Model of Obstructive Jaundice Stimulated by Lipopolysaccharide," Peptides, 2006, pp. 2592-2599, vol. 27.

Giacometti, A. et al., "The Antimicrobial Peptide BMAP-28 Reduces Lethality in Mouse Models of Staphylococcal Sepsis," American Journal of Respiratory and Critical Care Medicine, 2004, pp. 2485-2490, vol. 32, No. 12.

Giacometti, A. et al., Cathelicidin Peptide Sheep Myeloid Antimicrobial Peptide-29 Prevents Endotoxin-Induced Mortality in Rat Models of Septic Shock, American Journal of Respiratory and Critical Care Medicine, 2004, pp. 187-194, vol. 169.

Glenn, G.M. et al., "Skin Immunization Made Possible by Cholera Toxin," Nature, Feb. 26, 1998, p. 851, vol. 391.

Gonzalez, A. et al., Letters to the Editor, J. Hosp. Infect., 2003 pp. 156-157, vol. 55.

Guichard, G. et al., "Antigenic Mimicry of natural L-Peptides with Retro-Inverso-Peptidomemitics," Proc. Natl. Acad. Sci., USA, 1994, pp. 9765-9769, vol. 91, No. 21.

Hancock, R.E.W. et al., "Antimicrobial and Host-Defense Peptides as New Anti-Infective Therapeutic Strategies," Nature Biotechnology, Dec. 2006, pp. 1551-1557, vol. 24, No. 12.

(56) References Cited

OTHER PUBLICATIONS

Hancock, R.E.W. et al., "The Role of Cationic Antimicrobial Peptides in Innate Host Defences," Trends in Microbiology, Sep. 2000, pp. 402-410, vol. 8, No. 9.

Hanes, J. et al., "New Advances in Microsphere-Based Single-Dose Vaccines," Advanced Drug Delivery Reviews, 1997, pp. 97-119, vol. 28.

Healy, V.L. et al., "Active-Site Mutants of the VanC2 D-alanyl-D-serine Ligase, Characteristic of One Vancomycin-Resistant Bacterial Phenotype, Revert Towards Wild-Type D-alanyl-D-alanine Ligases," Chemistry & Biology, 1998, pp. 197-207, vol. 5, No. 4.

Heilborn, J.D. et al., "The Cathelicidin Anti-Microbial Peptide LL-37 is Involved in Re-Epithelialization of Human Skin Wounds and is Lacking in Chronic Ulcer Epthelium," The Journal of Investigative Dermatology, Mar. 2003, pp. 379-389, vol. 120, No. 3.

Hein, W.R. et al., "A Road Less Travelled: Large Animal Models in Immunological Research," Nature Reviews Immunology, Jan. 2003, pp. 79-84, vol. 3.

Hemmi, H. et al., "A Toll-Like Receptor Recognizes Bacterial DNA," Nature, Dec. 2000, pp. 740-745, vol. 408.

Horn, T. et al., "Synthesis of Oligonucleotides on Cellulose. Part II: Design and Synthesis Strategy to the Synthesis of 22 Oligodeoxynucleotides Coding for Gastric Inhibitory Polypeptide (GIP)," Nucleic Acids Research, Symposium Series No. 7, 1980, pp. 225-232.

Hruby, V.J. et al., "Synthesis of Oligopeptide and Peptidomimetic Libraries," Current Opinion in Chemical Biology, 1997, pp. 114-119, vol. 1.

Jiang, Z. et al., "Measuring Conservation of Contiguous Sets of Autosomal Markers on Bovine and Procine Genomes in Relation to the Map of the Human Genome," Genome, 2002, pp. 769-776, vol. 45.

Klinman, D.M. et al., "Immunotherapeutic Uses of CpG Oligodeoxynucleotides," Nature Reviews Immunology, Apr. 2004, pp. 1-10, vol. 4.

Kroll, D.J. et al., A Multifunctional Prokaryotic Protein Expression System: Overproduction, Affinity Purification, and Selective Detection, DNA and Cell. Biology, Nov. 5, 1993, pp. 441-453, vol. 12, No. 5.

Kurosaka, K. et al., "Mouse Cathelin-Related Antimicrobial Peptide Chemoattracts Leukocytes Using Formyl Peptide Receptor-Like 1/Mouse Formyl Peptide Receptor-Like 2 as the Receptor and Acts as an Immune Adjuvant," J. Immunol., 2005, pp. 6257-6265, vol. 174.

Kwakman, P.H.A. et al, "Treatment and Prevention of *Staphylococcus epidermidis* Experimental Biomaterial-Associated Infection by Bactericidal Peptide 2," Antimirobial Agents and Chemotherapy, Dec. 2006, pp. 3977-3983, vol. 50, No. 12.

Langer, R., "New Methods of Drug Delivery," Science, Sep. 28, 1990, pp. 1527-1533, vol. 249.

Lau, Y.E. et al., "Interaction and Cellular Localization of the Human Host Defense Peptide LL-37 with Lung Epithelial Cells," Infection and Immunity, Jan. 2005, pp. 583-591, vol. 73, No. 1.

Lee, D.L. et al., "Effects of Single D-Amino Acid Substitutions on Disruption of β-Sheet Structure and Hydrophobicity in Cyclic 14-Residue Antimicrobial Peptide Analogs Related to Gramicidin S," J. Pept. Res., Feb. 2004, pp. 69-84, vol. 63, No. 2.

Lehrer, R.I. et al., "Cathelicidins: A Family of Endogenous Antimicrobial Peptides," Current Opinion in Hematology, 2002, pp. 18-22, vol. 9.

Marr, A.K. et al., "Antibacterial Peptides for Therapeutic Use: Obstacles and Realistic Outlook," Current Opinion in Pharmacology, 2006, pp. 468-472, vol. 6.

McPhee, J.B. et al., "Function and Therapeutic Potential of Host Defence Peptides," Journal of Peptide Science, 2005, pp. 677-687, vol. 11.

Merrifield, R.B. et al., "Retro and Retroenantio Analogs of Cecropin-Melittin Hybrids," Proc. Natl. Acad. Sci. USA, Apr. 1995, pp. 3449-3453, vol. 92.

Merrifield, B., "Concept and Early Development of Solid-Phase Peptide Synthesis," Methods in Enzymology, 1997, pp. 3-13, vol. 289.

Mookherjee, N. et al., "Bovine and Human Cathelicidin Cationic Host Defense Peptides Similarly Suppress Transcriptional Responses to Bacterial Lipopolysaccharide," J. Leokocyte. Biol., 2006, pp. 1563-1574, vol. 80.

Mookherjee, N. et al., "Modulation of the TLR-Mediated Inflammatory Response by the Endogenous Human Host Defense Peptide LL-37," J. Immunol., 2006, pp. 2455-2464, vol. 176.

Myers, E.W. et al., "Optimal Alignments in Linear Space," CABIOS, 1988, pp. 11-17, vol. 4, No. 1.

Mygind, P.H. et al., "Plectasin is a Peptide Antibiotic with Therapeutic Potential from a Saprophytic Fungus," Nature, Oct. 13, 2005, pp. 975-980, vol. 437.

Nagpal, S. et al., "Plasticity in Structure and Interactions is Critical for the Action of Indolicidin, an Antibacterial Peptide of Innate Immune Origin," Protein Sci., 2002, pp. 2158-2167, vol. 11, No. 9.

Needleman, S.B. et al., "A General Method Applicable to the Search for Similarities in the Amino Acid Sequence of Two Proteins," J. Mol. Biol., 1970, pp. 444-453, vol. 48.

Niyonsaba, F. et al., "Epithelial Cell-Derived Human β-Defensin-2 Acts as a Chemotaxin for Mast Cells Through a Pertussis Toxin-Sensitive and Phospholipase C-Dependent Pathway," International Immunology, 2002, pp. 421-426, vol. 14, No. 4.

Nizet, V. et al., "Innate Antimicrobial Peptide Protects the Skin from Invasive Bacterial Infection," Nature, Nov. 22, 2001, pp. 454-457, vol. 414.

Ong, P.Y. et al., "Endogenous Antimicrobial Peptides and Skin Infections in Atopic Dermatitis," N. Engl. J. Med., Oct. 10, 2002, pp. 1151-1160, vol. 347, No. 15.

Oren, Z. et al., "Selective Lysis of Bacteria but not Mammalian Cells by Diastereomers of Melittin: Structure—Function Study," Biochemistry, 1997, pp. 1826-1835, vol. 36.

Ostergaard, S. et al., "Peptomers: A Versatile Approach for the Preparation of Diverse Combinatorial Peptidomimetic Bead Libraries," Molecular Diversity, 1997, pp. 17-27, vol. 3.

Ostresh, J.M. et al., "Generation and Use of Nonsupport-Bound Peptide and Peptidomimetic Combinatorial Libraries," Methods in Enzymology, 1996, pp. 220-234, vol. 267.

Paul, A. et al., "Transdermal Immunization with Large Proteins by Means of Ultradeformable Drug Carriers," Eur. J. Immunol., 1995, pp. 3521-3524, vol. 25.

Pazgier, M et al., "Studies of the Biological Properties of Human β-Defensin 1," The Journal of Biological Chemistry, Jan. 19, 2007, pp. 1819-1829, vol. 282, No. 3.

PCT International Search Report and Written Opinion, PCT Application No. PCT/CA2008/001221, Oct. 22, 2008, 19 pages.

Pütsep, K. et al., "Deficiency of Antibacterial Peptides in Patients with morbus Kostmann: An Observation Study," Lancet, 2002, pp. 1144-1149, vol. 360.

Roberge, J.Y. et al., "A Strategy for a Convergent Synthesis of N-Linked Glycopeptides on a Solid Support," Science, Jul. 14, 1995, pp. 202-204, vol. 269.

Rosenfeld, Y. et al., "Endotoxin (Lipopolysaccharide Neutralization by Innate Immunity Host-Defense Peptides," Peptide Properties and Plausible Modes of Action, J. Biol. Chem., 2006, pp. 1636-1643, vol. 281, No. 3.

Ross, C.R. et al., The Antimicrobial Peptide PR-39 Has a Protective Effect Against HeLa Cell Apoptosis, Chem. Biol. Drug Des., 2007, pp. 154-157, vol. 70.

Scherf, T. et al. "Induced Peptide Confirmations in Different Antibody Complexes: Molecular Modeling of the Three-Dimensional Structure of Peptide-Antibody Complexes using NMR-Derived Distance Restraints," Biochemistry, 1992, pp. 6884-6897, vol. 31.

Schwenger, V. et al., "Treatment of Life-Threatening Multiresistant Staphylococcal and Enterococcal Infections in Patients with End-Stage Renal Failure with Quinupristin/Dalfopristin: Preliminary Report," Infection, 2002, pp. 257-261, vol. 30, No. 5.

Scott, M.G. et al., "An Anti-Infective Peptide that Selectively Modulates Innate Immune Response," Nature Biotechnology, Apr. 2007, pp. 465-472, vol. 25, No. 4.

(56) References Cited

OTHER PUBLICATIONS

Scott, M.G. et al., "The Human Antimicrobial Peptide LL-37 Is a Multifunctional Modulator of Innate Immune Responses," The Journal of Immunology, 2002, pp. 3883-3891, vol. 169.

Scott, M.G. et al., "Cutting Edge: Cationic Antimicrobial Peptides Block the Binding of Lipopolysaccharide (LPS) to LPS Binding Protein," The Journal of Immunology, 2000, pp. 549-553, vol. 164.

Skerlavaj, B. et al., "Biological Characterization of Two Novel Cathelicidin-Derived Peptides and Identification of Structural Requirements for Their Antimicrobial and Cell Lytic Activities," The Journal of Biological Chemistry, Nov. 8, 1996, pp. 28375-28381, vol. 271, No. 45.

Song, Z. et al., "Effects of Intratracheal Administration of Novispririn G10 on a Rat Model of Mucoid *Pseudomonas aeruginosa* Lung Infection," Antimicrobial Agents and Chemotherapy, Sep. 2005, pp. 3868-3874, vol. 49, No. 9.

Steinstraesser, L et al., "Protegrin-1 Enhances Bacterial Killing in Thermally Injured Skin," Crit. Care Med., 2001, pp. 1431-1437, vol. 29, No. 7.

Steinstraesser, L., "Sepsis—New Strategies with Host Defense Peptides?" Crit. Care Med., 2004, pp. 2555-2556, vol. 32, No. 12.

Subbalakshmi, C. et al., "Mechanism of Antimicrobial Action of Indolicidin," FEMS Microbiology Letters, 1998, pp. 91-96, vol. 160.

Tenover, F.C. et al., "Vancomycin-Resistant Staphylococci and Enterococci: Epidemiology and Control," Current Opinion in Infectious Diseases, 2005, pp. 300-305, vol. 18.

Tjabringa, G.S. et al., "The Antimicrobial Peptide LL-37 Activates Innate Immunity at the Airway Epithelial Surface by Transactivation of the Epidermal Growth Factor Receptor," J. Immunol., 2003, pp. 6690-6696, vol. 171.

Veldhuizen, E.J.A. et al., "Porcine β-Defensin 2 Displays Broad Antimicrobial Activity Against Pathogenic Intestinal Bacteria," Molecular Immunology, 2008, pp. 386-394, vol. 45.

Williams, G. et al., "Dissection of the Extracellular Human Interferon γ Receptor α-Chain into Two Immunoglobulin-like Domains. Production in an *Escherichia coli* Thioredoxin Gene Fusion Expression System and Recognition by Neutralizing Antibodies," Biochemistry, 1995, pp. 1787-1797, vol. 34.

Wilson, C.L. et al., "Regulation of Intestinal α-Defensin Activation by the Metalloproteinase Matrilysin in Innate Host Defense," Science, 1999, pp. 113-117, vol. 286.

Wilson, B.A. et al., "Ecology and Physiology of Infectious Bacteria—Implications for Biotechnology," Current Opinion in Biotechnology, 2002, pp. 267-274, vol. 13.

Wu, M. et al., "Improved Derivatives of Bactenecin, a Cyclic Dodecameric Antimicrobial Cationic Peptide," Antimicrobial Agents and Chemotherapy, May 1999, pp. 1274-1276, vol. 43, No. 5.

Xiao, Y et al., "Structure-Activity Relationships of Fowlicidin-1, a Cathelicidin Antimicrobial Peptide in Chicken," The FEBS Journal, 2006, pp. 2581-2593, vol. 273.

Yang, B.D. et al., "LL-37, the Neutrophil Granule- and Epithelial Cell-Derived Cathelicidin, Utilizes Formyl Peptide Receptor-like 1 (FPRL1) as a Receptor to Chemoattract Human Peripheral Blood Neutrophils, Monocytes, and T Cells," The Journal of Experimental Medicine, Oct. 2, 2000, pp. 1069-1074, vol. 192.

Zaiou, M. et al., "Cathelicidins, Essential Gene-Encoded Mammalian Antibodies," J. Mol. Med., 2002, pp. 549-561, vol. 80.

Zaiou, M. et al., "Antimicrobial and Protease Inhibitory Functions of the Human Cathelicidin (hCAP18/LL-37) Prosequence," J. Invest. Dermatol., May 2003, pp. 810-816, vol. 120, No. 5.

Zanetti, M. Cathelicidins, Multifunctional Peptides of the Innate Immunity, J. Leukoc. Biol., 2004, pp. 39-48, vol. 75, No. 1.

Zasloff, M., "Antimicrobial Peptides of Multicellular Organisms," Nature, Jan. 24, 2002, pp. 389-395, vol. 415.

Zhang, G. et al., "Porcine Antimicrobial Peptides: New Prospects for Ancient Molecules of Host Defense," Vet. Res., 2000, pp. 277-296, vol. 31.

\* cited by examiner

FIGURE 1A

| Host Defense Peptide | Sequence | SEQ ID Number |
|---|---|---|
| BMAP-28 | GlyLeuArgSerLeuGlyArgLysIleLeuArgAlaTrp<br>LysLysTyrGlyProIleIleValProIleIleArgIleGly | 1 |
| RI-BMAP-28 | (D)Gly(D)Ile(D)Arg(D)Ile(D)Pro(D)Val<br>(D)Ile(D)Ile(D)Pro(D)Gly(D)Tyr(D)Lys(D)Lys<br>(D)Trp(D)Ala(D)Arg(D)Leu(D)Ile(D)Lys(D)Arg<br>(D)Gly(D)Leu(D)Ser(D)Arg(D)Leu(D)Gly | 2 |

FIGURE 1B
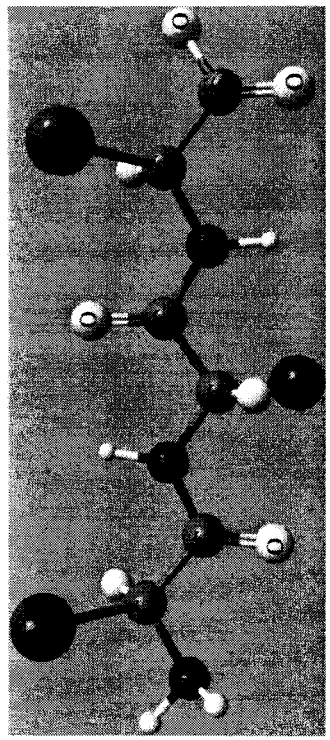
L-Peptide
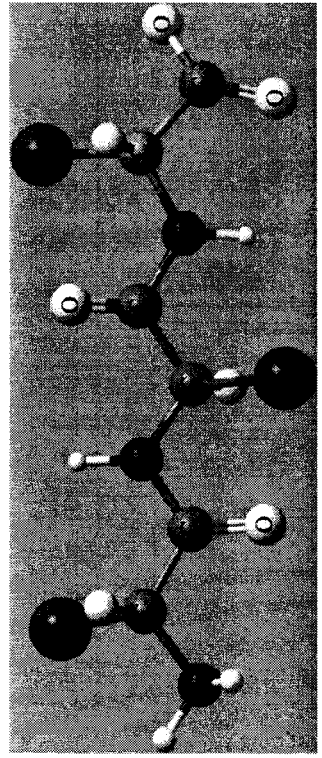
RI-Peptide
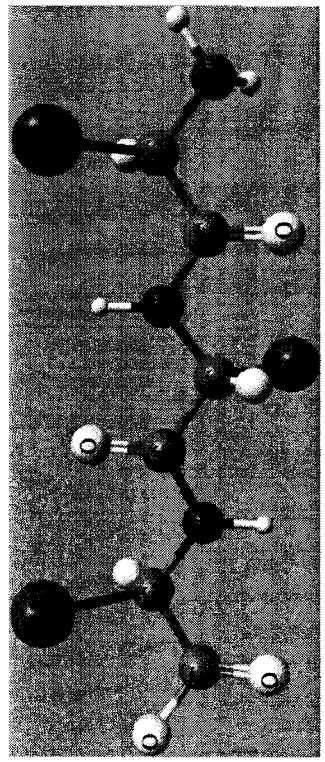
RI-Peptide (inverted 180°)

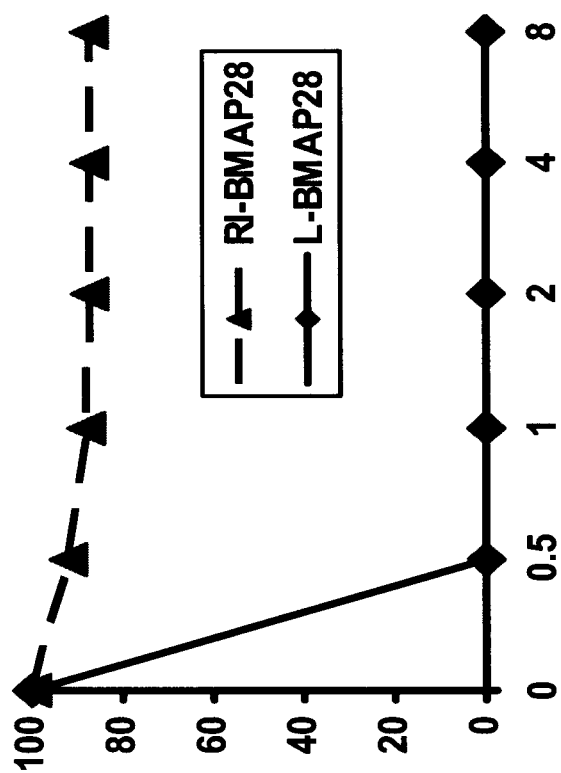

IMMUNOMODULATORY COMPOSITIONS AND METHODS FOR TREATING DISEASE WITH MODIFIED HOST DEFENSE PEPTIDES

CROSS-REFERENCE TO RELATED APPLICATIONS

This application claims the benefit of priority to U.S. provisional patent application Ser. No. 60/946,888, filed Jun. 28, 2007, and U.S. provisional patent application Ser. No. 60/989,392, filed Nov. 20, 2007, the disclosures of which are incorporated by reference in their entirety.

FIELD

The invention generally relates to compositions and methods for modulating an immune response in a vertebrate subject. Compositions and methods are provided which comprise administering a modified host defense peptide to the vertebrate subject in an amount effective to activate the immune response for a variety of therapeutic objectives in the vertebrate subject, wherein the modified host defense peptide is modified either completely or partially to D-amino acids, or is inverted in amino acid sequence from an amino terminus to a carboxy terminus, or both modifications, when compared to a host defense peptide. Compositions and methods are provided which comprise administering a modified host defense peptide to the vertebrate subject in an amount effective to activate the immune response to serve as vaccination adjuvants.

BACKGROUND

The extensive application of conventional antibiotics has served as a selection pressure to drive the evolution of multiple drug resistant strains, Trevor et al., *Curr. Opin. Infect. Dis.* 18: 300-305, 2005. The rapid emergence of antibiotic-resistant bacteria, including those that are resistant to "last resort" antibiotics such as vancomysin, is one of the greatest challenges facing modern medicine and has provoked the exploration for new antimicrobial agents and strategies. A new paradigm in the treatment of infections is through activation of the innate immune system rather than, or in addition to, direct attack on the microbe as employed by conventional antibiotics, Finlay et al., *Nat. Rev. Microbiol.* 2: 497-504, 2004.

Host defense peptides (HDPs) have an evolutionary history of combating infections and represent a conserved mechanism of innate immune defense that is present in virtually all forms of life. In general HDPs range in size from twelve to fifty amino acids, carry a net positive charge and consist of approximately 50% hydrophobic residues. Hancock et al., *Trends Microbiol.* 8: 402-410, 2000. These peptides are an essential component of immune defense as their absence through either genetic knock-out or disease renders the host more susceptible to infections. Nizet et al., *Nature* 414: 454-457, 2001; Wilson et al., *Science* 286: 113-117, 1999; Ganz et al., *J. Clin. Invest.* 82: 552-556, 1988; Ong et al., *N. Engl. J. Med.* 347: 1151-1160, 2002; Putsep et al., *Lancet* 360: 1144-1149, 2002. Conversely HDP administration in animal models can prevent and treat bacterial infections, while offering protection from sepsis. Song et al., *Antimicrob Agents Chemother.* 49: 3868-74, 2005; Kwakman et al.; *Antimirob Agents Chemother.* 50: 3977-83, 2006, Giacometti et al., *Crit. Care Med.* 32: 2555-2556, 2004; Fukumoto et al., *Pediatr. Surg. Int.* 21: 20-24, 2005; Cirioni et al., *Antimicrob. Agents Chemother.* 50: 1672-1679, 2006.

The initial appreciation of the therapeutic potential of HDPs was from the perspective of their direct antimicrobial activity. While the specific details of direct antimicrobial action have yet to be conclusively determined, it is hypothesized that the majority, although not all, of HDPs kill bacteria through interactions with the bacterial membrane that ultimately lead to cell lysis. Subbalakshmi et al., *FEMS Microbiol Lett.* 160: 91-96, 1998; Brotz, H. et al., 42: 154-160, 1998, McPhee et al., *J. Pept. Sci.* 11: 677-687, 2005. That such a diverse range of HDPs have antimicrobial activity against a broad spectrum of bacteria, including Gram-negative and Gram-positive strains, suggests that the antimicrobial mechanism is dependent upon general characteristics of these molecules and their targets. Specifically, the positive charge of HDPs is hypothesized to be an essential feature in targeting the action of these molecules against bacterial membranes whose outer leaflet is rich in negatively-charged phospholipids, as opposed to the outer leaflet of plant and animal membranes which favor neutral lipids, McPhee et al., *J. Pept. Sci.* 11: 677-687, 2005.

There has been an emerging appreciation however that the biological action, and perhaps therapeutic potential, of these molecules extends beyond the ability to disrupt bacterial membranes. Indeed the physiological significance of HDP antimicrobial activity has been called into question as levels of expression of many of these peptides are below their antimicrobial thresholds and this activity is often suppressed in serum and by physiological concentrations of monovalent and divalent ions. Bowdish et al., *Curr. Protein Pept. Sci.* 6: 1-17, 2005; Bowdish et al., *Antimicrob. Agents Chemother.* 49: 1727-1732, 2005. Furthermore that peptides that do not possess antimicrobial activity still offer protection from bacterial challenges in animal models indicates that these molecules counter infections by influencing host cell process rather than direct antimicrobial activity. Scott et al., *Nature Biotech.* 25: 465-472, 2007; published online Mar. 25, 2007.

Emerging evidence suggests that HDPs assist in clearing infections by activating host cell processes associated with innate immunity, adaptive immunity and inflammation. HDPs have been shown to have involvement in a broad range of biological effects associated with immune functions including the up-regulation of chemokines/chemokines and their receptors, recruitment of leukocytes to sites of infection, stimulation of histamine release from mast cells, angiogenesis, dendritic cell maturation and wound healing. Bowdish et al., *Curr. Protein Pept. Sci.* 6: 1-17, 2005; Bowdish et al., *Antimicrob. Agents Chemother.* 49: 1727-1732, 2005; Hancock et al., *Nat. Biotech.* 24: 1551-1557, 2006; Scott et al., *J. Immunol.* 169: 3883-3891, 2002; Heilborn et al., *J. Invest. Dermatol.* 120: 379-389, 2003; Marr et al., *Curr. Opin. Pharm.* 6: 468-472, 2006. HDPs have also been shown to function as anti-endotoxic agents by modulating the deleterious consequences of inflammation and limiting the development of sepsis, Giacometti et al., *Crit. Care Med.* 32: 2555-2556, 2004; Fukumoto et al., *Pediatr. Surg. Int.* 21: 20-24, 2005; Cirioni et al., *Antimicrob. Agents Chemother.* 50: 1672-1679, 2006; Zasloff, *Nature* 415: 389-395, 2002.

While HDPs have found application in the treatment of topical infections (gramicidin S and polymyxin B), and as food preservatives (nisin), they have yet to achieve success in the larger market of treatment of systemic infections. One of the key limitations to the development of therapeutic HDPs for systemic treatment of bacterial infections has been their prohibitive cost. For example, synthesis of one gram of a typical HDP, which is the average daily dose required for systemic HDP administration, costs in the range of $100-$600. Hancock et al., *Nat. Biotech.* 24: 1551-1557, 2006. By comparison production of an equal quantity of an aminoglycoside antibiotic costs approximately 80 cents. Marr et al., *Curr. Opin. Pharm.* 6: 468-472, 2006. The high cost of peptide synthesis is compounded by the sensitivity of these molecules to proteolytic degradation as the biological half-life of HDPs measures in minutes. Finlay et al., *Nat. Rev. Microbiol.* 2: 497-504, 2004. Peptide modifications that increase biological stability to reduce dose quantities and frequencies will result in corresponding decreases in the associated costs. One such strategy of peptidomimetic optimization is through retro-inversion.

Retro-inversed (RI) peptides are isomers of natural peptides in which the sequence is reversed and the chirality of each amino acid is inverted, Chorev et al., *TIBS* 13: 438-445, 1995; Fischer, *Curr. Prot. and Pept. Sci.* 4: 339-356, 2003. Peptides modified in this manner are predicted to maintain the same three-dimensional topology of side-chains as their natural counterparts and therefore have the potential to maintain the same biological activities. A key structural and functional distinction of the retroinversed molecules is that peptide bonds linking D-amino acids are poor substrates for proteolytic enzymes which greatly improves the biological stability of RI-peptides, Fauchere et al., *Adv. Drug. Res.* 23: 127-159, 1992.

The application of retro-inversion to biological peptides has been explored with largely mixed results, Chorev et al., *TIBS* 13: 438-445, 1995; Fischer, *Curr. Prot. and Pept. Sci.* 4: 339-356, 2003. The differential ability of RI-peptides to maintain the functional characteristics of their natural counterparts is likely a consequence of the structural complexity of individual peptide as well as the mechanism through which it exerts its biological action. For peptides whose biological functions are dependent upon interactions with chiral molecules, such as DNA or protein, the extent to which the main-chain peptide groups contribute to complex formation will likely predict the extent to which the modification will be tolerated.

Retroinversion of HDPs has been explored in a limited number of cases with the general conclusion that the modification results in retained or moderately improved antimicrobial activity, Merrifield et al., *Proc. Natl. Acad. Sci. USA* 88: 4240-4244, 1995. Importantly however these investigations were limited to consideration of antimicrobial, rather than immunomodulatory, activity. As antimicrobial activity is mediated through non-stereospecific interactions with bacterial membranes it would be anticipated to be much more tolerant to retroinversion. The more stringent criteria by which retroinversion will be evaluated in HDPs is through the ability to influence higher-order innate immune function through interaction with chiral host receptors.

The extensive application of conventional antibiotics has served as a selection pressure to drive the evolution of multiple drug resistant strains of bacteria and other infectious agents that can cause infectious disease. A need exists in the art for improved and effective therapeutic compounds for treatment of infectious diseases, e.g., bacterial and parasitic infectious disease, and inflammatory diseases.

SUMMARY

The invention generally relates to compositions and methods for modulating an immune response in a vertebrate subject. The ability of host defense peptides to activate innate immune responses to promote infection-resolving immunity, mediate direct antimicrobial action and modulate pro-inflammatory responses could introduce a new paradigm for 1) treatment of bacterial, viral and parasitic infections, 2) treatment of sepsis and other disorders associated with excessive inflammation and 3) as adjuvants to promote effective immune responses during vaccination. As such to view these molecules as the functional equivalents of conventional antibiotics underestimates the complexity of their biological action.

Compositions and methods are provided which comprise administering a modified host defense peptide to the vertebrate subject in an amount effective to activate/modulate the immune response for the purposes of either treatment of infections, limitation of inflammation or as vaccine adjuvants, wherein the modified host defense peptide is inverted in amino acid sequence from an amino terminus to a carboxy terminus or modified to one or more D-amino acids, or both modifications, when compared to a host defense peptide. The compositions and methods can be administered in an amount effective to reduce or eliminate an infectious disease in a vertebrate subject. The modified host defense peptide can have an adjuvant activity to stimulate an immune response against an infectious disease in the vertebrate subject. The infectious disease can be a bacterial, viral, fungal, or parasitic infectious disease. Compositions and methods are provided which comprise administering a modified host defense peptide to the vertebrate subject in an amount effective to inhibit the immune response and reduce host toxicity in the vertebrate subject. The compositions and methods can be administered in an amount effective to reduce or eliminate an inflammatory disease or sepsis in a vertebrate subject. Compositions and methods are provided which comprise administering a modified host defense peptide to the vertebrate subject in an amount effective to activate the immune response to serve as vaccination adjuvants.

The present study reports that a modified host defense peptide, wherein the modified host defense peptide is inverted in amino acid sequence from an amino terminus to a carboxy terminus or modified to one or more D-amino acids, or both modifications, when compared to a host defense peptide, for example, a retro-inversed form of BMAP-28 (RI-BMAP-28), which adopts a similar conformation as the natural peptide, is resistant to proteolytic degradation and has improved direct antimicrobial activity against a broad spectrum of bacteria. With respect to the ability to influence higher-order immune function, RI-BMAP-28 maintains the ability to mediate anti-endotoxic effects through alterations of host cell gene expression and release of pro-inflammatory cytokines. Unexpectedly the RI-BMAP-28 also has a significant reduction in cytotoxicity as compared to its natural counterpart. As the cytotoxicity of HDPs, and in particular BMAP-28, represents a significant limitation to their systemic administration this could be of significant consequence. The ability for retroinversion approaches to retain, or improve, biological functions, with increased biological stability and decreased toxicity, will advance the therapeutic potential of this, and potentially other, host defense peptides.

A method for modulating an immune response in a vertebrate subject in need thereof is provided which comprises administering a modified host defense peptide in an amount effective to activate the immune response in the vertebrate subject, wherein the modified host defense peptide is modified by at least one of: inversion in amino acid sequence from an amino terminus to a carboxy terminus, or modification to one or more D-amino acids, when compared to a host defense peptide. In one aspect, the modified host defense peptide is modified by all D-amino acids. In a further aspect, the modified host defense peptide is modified by inversion in amino acid sequence from an amino terminus to a carboxy terminus and by one or more D-amino acids. The host defense peptide includes, but is not limited to, BMAP-28. In one aspect, the host defense peptide can comprise an amino acid sequence of SEQ ID NO:1. The host defense peptide comprises an amino acid sequence having L-amino acids: NH$_2$-GLRSLGRKIL-RAWKKYGPIIVPIIRIG-COOH (SEQ ID NO:1). In a further aspect, the modified host defense peptide can have between 27 and about 50 amino acids and comprises an amino acid sequence of SEQ ID NO:2. A retroinverted host defense peptide comprises an amino acid sequence having D-amino acids: NH$_2$— GIRBPVIIPGYKKWARLIKRGLSRLG-COOH (SEQ ID NO:2). In a detailed aspect, the modified host defense peptide can consist of an amino acid sequence of SEQ ID NO:2. The modified host defense peptide can be optionally modified, said modification selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of CH$_3$CO, CH$_3$(CH$_2$)$_n$CO, C$_6$H$_5$CH$_2$CO, NH$_2$ and H$_2$N(CH$_2$)$_n$CO, wherein n=1-10. The modified host defense peptide can be optionally modified as a fusion protein or a polypeptide conjugated to carbohydrate or lipid.

The vertebrate subject can include, but is not limited to, mammalian, avian, reptilian, amphibian, osteichthyes, or chondrichthyes.

A retroinverted host defense peptide is provided which comprises between 8 and about 12 amino acids of an amino acid sequence of SEQ ID NO:2. For example, the retroinverted host defense peptide includes, but is not limited to, an amino acid sequence having D-amino acids: NH$_2$-GIRIIPVI-COOH, NH$_2$-IPGYKKWA-COOH, NH$_2$-RLIKRGLS-COOH, NH$_2$-IPVIIPGY-COOH, NH$_2$-KKWARLIK-COOH, NH$_2$-KRGLSRLG-COOH. Other variants of retroinverted host defense peptides are provided comprising between 8 and about 12 amino acids of an amino acid sequence of SEQ ID NO:2 are included.

The modified host defense peptide can decrease cytotoxicity to host cells in the vertebrate subject compared to cytotoxicity of a host defense peptide for example, a naturally-occurring host defense peptide. The modified host defense peptide can stimulate an immune response against an infectious disease in the vertebrate subject. In a further aspect, the modified host defense peptide has an adjuvant activity to stimulate an immune response against an infectious disease in the vertebrate subject. The infectious disease can be a bacterial infectious disease, for example, a Gram-negative bacterial disease or a Gram-positive bacterial disease. The bacterial infectious disease can be an antibiotic resistant bacterial infectious disease. The infectious disease can be a viral disease, a fungal disease, or a parasitic disease. The bacterial infectious disease can include, but is not limited to, *Bacillus, Listeria, Staphylococcus, Streptococcus, Enterococcus, Clostridium,* or *Mycoplasma*. The bacterial infectious disease can include, but is not limited to, *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis,* or *Salmonella typhi*. The fungal infectious disease can include, but is not limited to, *Candida albicans* or *Cryptococcus neoformans*.

A method for modulating an immune response in a vertebrate subject in need thereof is provided which comprises administering a modified host defense peptide in an amount effective to inhibit the immune response and reduce host cell toxicity in the vertebrate subject, wherein the modified host defense peptide is modified by at least one of: inversion in amino acid sequence from an amino terminus to a carboxy terminus, or modification to one or more D-amino acids, when compared to a host defense peptide. The host defense peptide includes, but is not limited to, BMAP-28. In one aspect, the host defense peptide can comprise an amino acid sequence of SEQ ID NO:1. In a further aspect, the modified host defense peptide can have between 27 and about 50 amino acids and comprises an amino acid sequence of SEQ ID NO:2. In a detailed aspect, the modified host defense peptide can consist of an amino acid sequence of SEQ ID NO:2. A retroinverted host defense peptide is provided which comprises between 8 and about 12 amino acids of an amino acid sequence of SEQ ID NO:2.

The modified host defense peptide can decrease cytotoxicity to host cells in the vertebrate subject compared to cytotoxicity of a host defense peptide, for example, a naturally-occurring host defense peptide. The modified host defense peptide can reduce endotoxin activity in the vertebrate subject. The modified host defense peptide can reduce inflammatory disease or sepsis in the vertebrate subject. The inflammatory disease can be caused by arthritis, rheumatoid arthritis, osteoarthritis, spondylitis, gout, vasculitis, Crohn's disease, irritable bowel syndrome. The inflammatory disease can be associated with acute or chronic pain.

An isolated modified host defense peptide is provided having between 27 and about 50 amino acids, wherein said peptide comprises an amino acid sequence of SEQ ID NO:2. In one aspect, the peptide consists of the sequence amino acid sequence of SEQ ID NO:2. A composition is provided comprising the modified host defense peptide and a pharmaceutically acceptable carrier. A modified host defense peptide is provided which comprises between 8 and about 12 amino acids of an amino acid sequence of SEQ ID NO:2. The modified host defense peptide can be optionally modified, wherein the modification is selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of CH$_3$CO, CH$_3$(CH$_2$)$_n$CO, C$_6$H$_5$CH$_2$CO and H$_2$N(CH$_2$)$_n$CO, wherein n=1-10. The isolated modified host defense peptide can be optionally modified as a fusion protein or a polypeptide conjugated to carbohydrate or lipid.

BRIEF DESCRIPTION OF THE DRAWINGS

FIG. 1 shows structure and sequence of peptides and the retroinversed counterparts.

FIG. 2 shows RI-BMAP-28 is resistant to proteolytic degradation.

DETAILED DESCRIPTION

Figure 3:
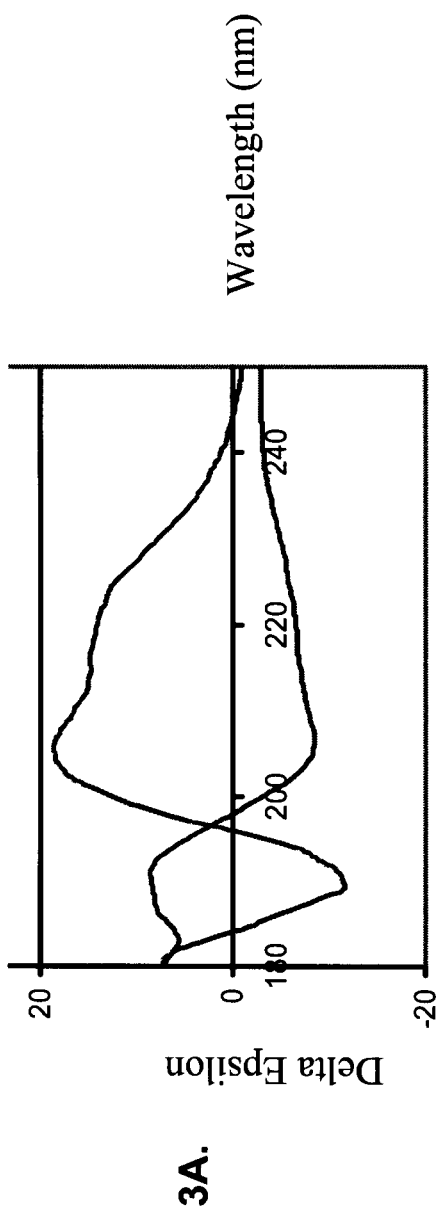
FIG. 3 shows RI-BMAP-28 adopts a similar pattern of secondary structure as BMAP-28.

The invention generally relates to compositions and methods for modulating an immune response in a vertebrate subject. Compositions and methods are provided which comprise administering a modified host defense peptide to the vertebrate subject in an amount effective to activate or modulate the immune response in the vertebrate subject, wherein the modified host defense peptide is inverted in amino acid sequence from an amino terminus to a carboxy terminus or modified to one or more D-amino acids, or both modifications, when compared to a host defense peptide. The compositions and methods can be administered in an amount effective to reduce or eliminate an infectious disease in a vertebrate subject. The modified host defense peptide can have an adjuvant activity to stimulate an immune response against an infectious disease in the vertebrate subject. The infectious disease can be a bacterial, viral, fungal, or parasitic infectious disease. Compositions and methods are provided which comprise administering a modified host defense peptide to the vertebrate subject in an amount effective to inhibit the immune response in the vertebrate subject. The compositions and methods can be administered in an amount effective to reduce or eliminate an inflammatory disease or sepsis in a vertebrate subject. Compositions and methods are provided which comprise administering a modified host defense peptide to the vertebrate subject in an amount effective to activate the immune response to serve as vaccination adjuvants.

While initially characterized for their ability to mediate direct antimicrobial activity there is an emerging appreciation that host defense peptides serve a higher-order function by serving as signaling and regulatory molecules for the host immune system. It has been demonstrated that host defense peptides are involved in a broad range of biological effects associated with immune functions including the up-regulation of chemokines/chemokines and their receptors, recruitment of leukocytes to sites of infection, stimulation of histamine release from mast cells, angiogenesis, dendritic cell maturation, wound healing and modulation of inflammation responses. The ability of host defense peptides to influence immune cells and processes associated with either innate and adaptive immunity, including those listed as well as others, is collectively referred to as their immunomodulatory function. The immunomodulatory functions of the host defense peptides has led to their application and demonstrated potential to: 1) treat and prevent bacterial, viral and fungal infections, 2) treat inflammatory disorders such as sepsis and 3) function as adjuvants. An adjuvant is defined here as an agent which does not have any specific affect in and of itself but has value through the ability to stimulate the immune system to increase the response to a vaccine.

Some key limitations to the therapeutic administration of host defense peptides for these three objectives are their biological instability and host cell toxicity. Here we demonstrate that retro-inversion of host defense peptides dramatically increases biological stability, reduces host cytotoxicity while maintaining the same biological activity as the natural counterpart. As such this modification is anticipated to dramatically increase the therapeutic potential of this class of peptides.

The antimicrobial, immune-stimulatory and anti-endotoxin activities of host defense peptides (HDPs) offer considerable potential for their application as antibiotics, anti-endotoxic agents and adjuvants. While HDPs have demonstrated efficacy as topical antimicrobials their application in the treatment of systemic infections has been limited by their prohibitive cost. Modifications that improve biological stability to reduce dose quantities and frequencies are therefore of considerable value. A potential approach is through retro-inversion (RI) in which the sequence of a natural peptide is reversed and synthesized from D-amino acids. Peptides modified in this manner are predicted to maintain side chain topology, hence biological activity, but with resistance to proteolytic degradation. HDPs are a functionally challenging test for RI approaches as these molecules are anticipated to have unique structural specificities for each of their biological activities. Using the example of a bovine myeloid antimicrobial peptide, BMAP-28, the present study reports that the retro-inverted isomer adopts the same conformation as the natural peptide, is resistant to proteolytic degradation and has improved antimicrobial activity. RI-BMAP-28 also maintains anti-endotoxin function as physiological concentrations of the peptide modulate inflammation at the levels of gene expression and cytokine release in LPS-stimulated monocytes and peripheral blood mononuclear cells respectively. Unexpectedly the cytotoxicity of BMAP-28 to host cells is dramatically reduced as a consequence of the modification. Collectively, retro-inversion methodologies advance the therapeutic potential of this, and potentially other, HDPs.

To determine the ability of a retro-inversed HDP to perform its full spectrum of biological activities the present study focused on bovine myeloid antimicrobial peptide, (BMAP-28) a 27 amino acid proteolytic product of the antibacterial peptide BMAP-28 precursor protein. BMAP-28 has antimicrobial activity at micromolar concentrations against a range of Gram-negative and -positive bacterial clinical isolates, including antibiotic-resistant strains, Benincasa et al., *Peptides* 24: 1723-1731, 2003, and retains these activities in the presence of physiological salt concentrations, Skerlavaj et al., *J. Biol. Chem.* 271: 28375-28381, 1996. BMAP-28 also has antiviral activity, providing protection against human simplex virus type I, Benincasa et al., *Peptides* 24: 1723-1731, 2003, as well as fungicidal activity Benincasa et al., *J. Antimicrob. Chemother.* 58: 950-959, 2006. BMAP-28 efficiently protects mice from lethal i.p. infections in an acute peritonitis model and reduces lethality in mouse models of staphylococcal sepsis at peptide doses lower than the host toxic threshold, re-enforcing their potential for therapeutic applications, Giacometti et al., *Crit. Care Med.* 32: 2555-2556, 2004; Benincasa et al., *Peptides* 24: 1723-1731, 2003; Skerlavaj et al., *J. Biol. Chem.* 271: 28375-28381, 1996; Benincasa et al., *J. Antimicrob. Chemother.* 58: 950-959, 2006. While the involvement of BMAP-28 in the modulation of innate immune responses hasn't been studied in detail, other bovine cathelicidins, such as BMAP-27, have been shown to possess immunomodulatory activity, Mookherjee et al., *J. Leokocyte. Biol.* 80:1-12, 2006.

It is to be understood that this invention is not limited to particular methods, reagents, compounds compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Bacterial resistance to conventional antibiotics has become commonplace, resulting in escalating numbers of life-threatening infections, Fernandez et al., *Int. J. Infect. Dis.* 7: 46-52, 2003; Wilson et al., *Curr. Opin. Biotechnol.* 13: 267-274, 2002; Schwenger, 2002 Infection 30, 257-261; Gonzalez et al., *J. Hosp. Infect.* 55: 156-157, 2003; Healy et al., C. T. *Chem. Biol.* 5: 197-207, 1998. Recent studies of cationic peptides as mediators of innate host defense have shown that, unlike pharmacologic antibiotics, these native host defense molecules have maintained broad-spectrum antimicrobial activity and resisted most microbial strategies for resistance, Zhang et al., *Vet. Res.* 31: 277-296, 2000; Zaiou et al., *J. Mol. Med.* 80: 549-561, 2002. These observations suggest that antimicrobial peptides can be attractive alternatives to current antibiotic regimens in select disease situations. Cathelicidins are a diverse family of cationic peptides with broad-range antimicrobial ability. Whereas humans and rodents have a single cathelicidin, many mammals have duplicated the cathelicidin gene to produce several unique C-terminal antimicrobial peptides with structures that vary from -helical to -sheet to rich in single amino acids, Zaiou et al., *J. Invest. Dermatol.* 120: 810-816, 2003; Lehrer, et al., *Curr. Opin. Hematol.* 9: 18-22, 2002; Gallo et al., *J. Allergy Clin. Immunol.* 110, 823-831, 2002. It is unknown whether the presence of multiple cathelicidins found in animals such as the pig and cow provides a benefit to these vertebrate species. However, mice generated to be deficient in their sole cathelin-related antimicrobial peptide (mCRAMP) develop significantly larger group A *Streptococcus* (GAS) skin lesions, compared with their wild-type littermates, Nizet et al., *Nature* 414: 454-457, 2001, and inhibiting activation of antimicrobial peptides increases bacterial growth in pigs, Cole et al., 97: 297-304, 2001, and mice, Wilson et al., *Science* 286: 113-117, 1999. Taken together, these observations support an essential role for antimicrobial peptides in defense against infection.

"A host defense peptide" refers to a peptide with antimicrobial, immune-modulator, and anti-endotoxin properties which can be used to treat bacterial, viral, parasitic, or fungal infectious disease, as adjuvants to increase vaccination efficacy, and as an anti-inflammatory agent against inflammatory disease or sepsis. Examples of host defense peptides include, but are not limited to, BMAP-28, IDR-1 (KSRIV-PAIPVSLL-NH$_2$), LL-37, indolicidin, or Bac2A. Scott et al., *Nature Biotech.* 25: 465-472, 2007; published online Mar. 25, 2007; Bowdish et al., *Antimicrob. Agents Chemother.* 49: 1727-1732, 2005; Bowdish et al., *J. Leukocyte Biology.* 77: 451-459, 2005.

Other examples of host defense peptides include, but are not limited to:

BMAP-27; Ghiselli R et al., *Peptides,* 27: 2592-2599, 2006.
Porcine beta-defensin 1; Elahi S et al., *Infect Immun* 74: 2338-2352, 2006.
PR-39; Ross et al., *Chem Biol Drug Des.* 70: 154-157, 2007.
Protegrin-1; Steinstraesser L et al., *Crit. Care Med* 29: 1431-1437, 2001.
Indolicidin; Bowdish D M et al., *Antimicrob Agents Chemother.* 49: 1727-1732, 2005.
Fowlicidin-3; Bommineni Y R et al., *FEBS J.* 274: 418-428, 2007.
Fowlicidin-1; Xiao Y et al., *FEBS J.* 273: 2581-2593, 2006.
Sheep myeloid antimicrobial peptide-29; Giacometti A et al., *Am J Respir Crit. Care Med.* 169: 187-194, 2004.
Human beta-defensin-2; Donnarumma G et al., *Peptides,* 2007 [Epub ahead of print].
Porcine beta-defensin-2; Veldhuizen et al., *Mol. Immunol.* 45: 386-394, 2008.
Human beta-defensin-3; Dhople V et al., *Biochim Biophys Acta.* 1758: 1499-1512, 2006.
Human beta-defensin-1; Pazgier M et al., *J Biol. Chem.* 282: 1819-1829, 2007.

"Bovine myeloid antimicrobial peptide" or "BMAP-28" refers to a 27 amino acid proteolytic product of the antibacterial peptide BMAP-28 precursor protein. BMAP-28 has antimicrobial activity at micromolar concentrations against a range of Gram-negative and Gram-positive bacterial clinical isolates, including antibiotic-resistant strains and retains these activities in the presence of physiological salt concentrations. BMAP-28 also has antiviral activity, providing protection against human simplex virus type I as well as fungicidal activity.

"A modified host defense peptide" or "a retro-inverted host defense peptide" or "a D-amino acid-modified host defense peptide" or "a modified host defense peptide modified by inversion in amino acid sequence from an amino terminus to a carboxy terminus" refers to peptides that are protease resistant and provide novel peptides with improved pharmacological properties. The improved properties are due to a reversed directionality (reversed from amino terminus to carboxy terminus) or inverted chirality (replacing one or more L-amino acids with D-amino acids) of the polypeptide molecules. Retro-peptides are directional isomers in which the sequence of the peptide is reversed from the amino terminus to the carboxy terminus with respect to the parent peptide. An inverted peptide can share the same sequence as the parent peptide but with inverted stereochemistry at the α carbon chiral centers, i.e., D-amino acids. Retroinverted peptides incorporate both of these modifications with reversal of sequence and utilization of D-amino acids. As such, the parent peptide is composed of L-amino acids in the sequence order (1, 2, 3, n) where residue 1 occupies the amino terminal position of the peptide. The corresponding retroinversed peptide is composed of D-amino acids in the sequence order (n, 3, 2, 1) where residue 1 now occupies the carboxy terminal position. When the retroinversed peptide is rotated by 180 degrees in the plane of the diagram the sequence of the modified peptide now reads (1, 2, 3, n) and the side chains superimpose in three-dimensional space with those of the parent peptide. RI peptides are therefore derivatives of natural peptides in which the relative side chain topology is maintained while the backbone termini and direction of the peptide bonds is reversed i.e., (—NH—CO—) versus (—CO—NH—). See, for example, FIGS. 1A and 1B.

"Adjuvant" refers to an agent which does not have any specific affect in and of itself but has value through the ability to stimulate the immune system to increase the response to a vaccine.

"Patient", "vertebrate subject" or "mammalian subject" are used herein and refer to mammals such as human patients and non-human primates, as well as experimental animals such as rabbits, rats, and mice, and other animals. Animals include all vertebrates, e.g., mammals and non-mammals, such as sheep, cows, dogs, cats, avian species, chickens, amphibians, reptiles, osteichthyes, or chondrichthyes.

"Treating" or "treatment" includes the administration of the compositions, compounds or agents of embodiments of the present invention to prevent or delay the onset of the symptoms, complications, or biochemical indicia of a disease, alleviating or ameliorating the symptoms or arresting or inhibiting further development of the disease, condition, or disorder (e.g., an infectious disease or inflammatory disease). "Treating" further refers to any indicia of success in the treatment or amelioration or prevention of the disease, condition, or disorder (e.g., a a infectious disease or inflammatory disease), including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of embodiments of the present invention to prevent or delay, to alleviate, or to arrest or inhibit development of the symptoms or conditions associated with a infectious disease or inflammatory disease. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a infectious disease or inflammatory disease but does not yet experience or exhibit symptoms, inhibiting the symptoms of a infectious disease or inflammatory disease (slowing or arresting its development), providing relief from the symptoms or side-effects of infectious disease or inflammatory disease (including palliative treatment), and relieving the symptoms of infectious disease or inflammatory disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

A "naturally-occurring" nucleic acid molecule refers to an RNA or DNA molecule having a nucleotide sequence that occurs in nature (e.g., encodes a natural protein).

A "naturally-occurring" polypeptide or protein refers to a polypeptide molecule having an amino acid sequence that occurs in nature (e.g., encodes a natural protein).

"Gene" and "recombinant gene" refer to nucleic acid molecules which include an open reading frame encoding a modified host defense peptide, e.g., a D-amino acid modified and/or retro-inverted host defense peptide, preferably a vertebrate, mammalian, bovine, human, avian reptilian, amphibian, osteichthyes, or chondrichthyes peptide, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means a preparation of a modified host defense peptide, e.g., a D-amino acid modified and/or a retro-inverted host defense peptide having less than about 30%, 20%, 10% and more preferably 5% (by dry weight), of non-RI-HDP protein (also referred to herein as a "contaminating protein"). When the retro-inverted host defense peptide, or biologically active portion thereof, is recombinantly produced, it is also preferably substantially free of culture medium, i.e., culture medium represents less than about 20%, more preferably less than about 10%, and most preferably less than about 5% of the volume of the protein preparation. Embodiments of the invention include isolated or purified preparations of at least 0.01, 0.1, 1.0, and 10 milligrams in dry weight.

A "non-essential" amino acid residue is a residue that can be altered from the wild-type sequence of the modified host defense peptide, e.g., a D-amino acid modified and/or a retro-inverted host defense peptide, without abolishing or more preferably, without substantially altering a biological activity, whereas an "essential" amino acid residue results in such a change. For example, amino acid residues that are conserved among the modified host defense peptides, e.g., a D-amino acid modified and/or a retro-inverted host defense peptide, those present in the domain of modified host defense peptide necessary for antimicrobial or anti-inflammatory activity, are predicted to be particularly not amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a modified host defense peptide, e.g., a D-amino acid modified and/or a retro-inverted host defense peptide is preferably replaced with another amino acid residue from the same side chain family. Alternatively, in another embodiment, mutations can be introduced randomly along all or part of a modified host defense peptide coding sequence, such as by saturation mutagenesis, and the resultant mutants can be screened for a modified host defense peptide biological activity to identify mutants that retain activity. Following mutagenesis of a modified host defense peptide, e.g., a D-amino acid modified and/or a retro-inverted host defense peptide, the encoded polypeptide can be expressed recombinantly and the activity of the protein can be determined.

A "biologically active portion" of a modified host defense peptide, e.g., RI-BMAP-28, includes a fragment of the modified host defense polypeptide which participates in an interaction between the modified host defense peptide molecule and an effector molecule, e.g., a bacterial membrane component. Biologically active portions of a modified host defense peptide, e.g., a D-amino acid modified and/or a retro-inverted host defense peptide, include peptides comprising amino acid sequences sufficiently identical to or derived from the amino acid sequence of the RI-HDP. Typically, biologically active portions comprise a domain or motif with at least one activity of the modified host defense peptide, e.g., RI-BMAP-28, including, e.g., anti-microbial activity, activating innate immune response, immunomodulatory activity, or lower cytotoxicity to host cells.

A biologically active portion of retro-inverted host defense peptide can be a polypeptide which is, for example, 10, 25, 50, 100, 200, or more, amino acids in length. Biologically active portions of a modified host defense peptide, e.g., RI-BMAP-28, can be used as targets for developing agents which modulate a a modified host defense peptide, e.g., a D-amino acid modified and/or a retro-inverted host defense peptide, activity as described herein.

Calculations of homology or sequence identity (the terms are used interchangeably herein) between sequences are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the modified host defense peptide, e.g., RI-BMAP-28, amino acid sequence, at least 10, preferably at least 20, more preferably at least 50, even more preferably at least 100 amino acid residues of the two sequences are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of embodiments of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to nucleic acid molecules encoding a modified host defense peptide, e.g., a D-amino acid modified and/or a retro-inverted host defense peptide, of embodiments of the invention. BLAST protein searches can be performed with the XBLAST program, score=50, wordlength=3 to obtain amino acid sequences homologous to modified host defense peptide, e.g., a D-amino acid modified and/or a retro-inverted host defense peptide, of embodiments of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

Particular modified host defense peptides, e.g., a D-amino acid modified and/or a retro-inverted host defense peptide polypeptides in embodiments of the present invention have an amino acid sequence sufficiently identical or substantially identical to the amino acid sequence of the modified host defense peptide, e.g., RI-BMAP-28. "Sufficiently identical" or "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as sufficiently or substantially identical.

"Misexpression or aberrant expression", as used herein, refers to a non-wild type pattern of gene expression, at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Peptides and Polypeptides

Embodiments of the invention provide isolated or recombinant polypeptides comprising an amino acid sequence having at least 95%, 96%, 97%, 98%, 99% or more sequence identity to SEQ ID NO:2 over a region of at least about 100, 150, 200, 250, 300, 350, 400, 450, 500, 550, 600, 650, 700, 750, 800, 850, 900, 950, 1000, 1100 or more residues, or, the full length of the polypeptide, or, a polypeptide encoded by a nucleic acid of embodiments of the invention. Embodiments of the invention provide methods for preventing or treating a bacterial, viral, fungal, or parasitic infectious disease in a vertebrate subject comprising administering to the vertebrate subject a modified host defense peptide, e.g., RI-BMAP-28. An embodiment of the invention also provides methods for screening compositions that inhibit the activity of, or bind to (e.g., bind to the active site), of bacterial membrane component or polypeptide. A modified host defense peptide, e.g., RI-BMAP-28, in an embodiment of the invention that stimulates anti-microbial activity, activates innate immune response, immunomodulatory activity, or lower cytotoxicity to host cells can reduce or eliminate bacterial, viral, fungal, or parasitic infectious disease or inflammatory disease.

In one aspect, an embodiments of the invention provides a modified host defense peptide, e.g., a D-amino acid modified and/or a retro-inverted host defense peptide (and the nucleic acids encoding them) where one, some or all of the modified host defense peptide, e.g., a D-amino acid modified and/or a retro-inverted host defense peptide, is replaced with substituted amino acids. In one aspect, an embodiments of the invention provides methods to disrupt the interaction with bacterial membrane components or proteins or with other proteins, in pathways related to entry or replication of infectious bacteria in the cells.

The retro-inverted host defense peptides in embodiments of the invention can be expressed recombinantly in vivo after administration of nucleic acids, as described above, or, they can be administered directly, e.g., as a pharmaceutical composition. They can be expressed in vitro or in vivo to screen for modulators of bacterial, viral, fungal, or parasitic infectious disease or inflammatory disease and for agents that can treat or ameliorate the disease.

Retro-inverted host defense peptides in embodiments of the invention can be isolated from natural sources, be synthetic, or be recombinantly generated polypeptides. Peptides and proteins can be recombinantly expressed in vitro or in vivo. The retro-inverted host defense peptides in embodiments of the invention can be made and isolated using any method known in the art. Retro-inverted host defense peptide in embodiments of the invention can also be synthesized, whole or in part, using chemical methods well known in the art. See e.g., Caruthers, *Nucleic Acids Res. Symp. Ser.* 215-223, 1980; Horn, *Nucleic Acids Res. Symp. Ser.* 225-232, 1980; Banga, A. K., Therapeutic Peptides and Proteins, Formulation, Processing and Delivery Systems Technomic Publishing Co., Lancaster, Pa., 1995. For example, peptide synthesis can be performed using various solid-phase techniques (see e.g., Roberge, *Science* 269: 202, 1995; Merrifield, *Methods Enzymol.* 289: 3-13, 1997) and automated synthesis can be achieved, e.g., using the ABI 431A Peptide Synthesizer (Perkin Elmer) in accordance with the instructions provided by the manufacturer.

The modified host defense peptide, e.g., a D-amino acid modified and/or a retro-inverted host defense peptide, in embodiments of the invention, as defined above, include all "mimetic" and "peptidomimetic" forms. The terms "mimetic" and "peptidomimetic" refer to a synthetic chemical compound which has substantially the same structural and/or functional characteristics of the polypeptides of embodiments of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the structure and/or activity of the mimetic. As with polypeptides of embodiments of the invention which are conservative variants, routine experimentation will determine whether a mimetic is within the scope of the invention, i.e., that its structure and/or function is not substantially altered. Thus, a mimetic composition is within the scope of the invention if, when administered to or expressed in a cell, it has a a modified host defense peptide, e.g., a D-amino acid modified and/or a retro-inverted host defense peptide, activity.

In one aspect, the polypeptide or peptidomimetic composition can be a dominant-negative mutant within the scope of the invention if it can inhibit bacterial infection or inflammation, e.g., be a dominant-negative mutant. The dominant negative mutant can be a peptide or peptide mimetic that can inhibit bacterial, viral, fungal, or parasitic infectious disease or inflammatory disease, or a nucleic acid composition, in the form of a DNA vector or gene therapy vector, that expresses a dominant-negative polypeptide that can inhibit bacterial, viral, fungal, or parasitic infectious disease or inflammatory disease. The dominant negative mutant can bind to a ligand of the bacterial membrane or a target, affecting ligand target interaction. The dominant negative molecule can act, for example, by blocking protein protein interactions, or by blocking interaction with the bacterial membrane.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholin-yl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for aspargine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy guanidino, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of guanidino and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a modified host defense peptide, e.g., a D-amino acid modified and/or a retro-inverted host defense peptide, in embodiments of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but which can additionally be referred to as the R- or S-form.

Various chemical modifications will improve the stability, bioactivity and ability of the modified host defense peptide to cross the blood brain barrier. One such modification is aliphatic amino terminal modification with a derivative of an aliphatic or aromatic acid, forming an amide bond. Such derivatives include, for example, $CH_3CO$, $CH_3(CH_2)_nCO$, $C_6H_5CH_2CO$, $NH_2$, and $H_2N(CH_2)_nCO$, wherein n=1-10. Another modification is carboxy terminal modification with a derivative of an aliphatic or aromatic amine/alcohol coupled to the modified host defense peptide via an amide/ester bond. Such derivatives include those listed above. The modified host defense peptides can also have both amino and carboxy terminal modifications, wherein the derivatives are independently selected from those listed above. The peptides can also be glycosylated, wherein either the alpha amino group or a D-Asn, or both, are modified with glucose or galactose. In another contemplated modification, selected backbone amide bonds are reduced (—NH—$CH_2$). Other modifications include N-methylation of selected nitrogens in the amide bonds and esters in which at least one of the acid groups on the peptide are modified as aromatic or aliphatic esters. Any combination of the above modifications is also contemplated.

Embodiments of the invention also provide polypeptides that are "substantially identical" to an exemplary polypeptide of embodiments of the invention. A "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a modified host defense peptide, e.g., a D-amino acid modified and/or a retro-inverted host defense peptide of embodiments of the invention, resulting in modification of the structure of the polypeptide, without significantly altering its biological activity. For example, amino- or carboxyl-terminal, or internal, amino acids which are not required for a modified host defense peptide, e.g., RI-BMAP-28, activity or interaction can be removed.

The skilled artisan will recognize that individual synthetic residues and polypeptides incorporating these mimetics can be synthesized using a variety of procedures and methodologies, which are well described in the scientific and patent literature, e.g., Organic Syntheses Collective Volumes, Gilman et al. (Eds) John Wiley & Sons, Inc., NY. Peptides and peptide mimetics of embodiments of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi, *Mol. Biotechnol.* 9: 205-223, 1998; Hruby, *Curr. Opin. Chem. Biol.* 1: 114-119, 1997; Ostergaard, *Mol. Divers.* 3: 17-27, 1997; Ostresh, *Methods Enzymol.* 267: 220-234, 1996. Modified peptides of embodiments of the invention can be further produced by chemical modification methods, see, e.g., Belousov, *Nucleic Acids Res.* 25: 3440-3444, 1997; Frenkel, *Free Radic. Biol. Med.* 19: 373-380, 1995; Blommers, *Biochemistry* 33: 7886-7896, 1994.

A modified host defense peptide, e.g., a D-amino acid modified and/or a retro-inverted host defense peptide in embodiments of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Amgen Inc., Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 34: 1787-1797, 1995; Dobeli, *Protein Expr. Purif.* 12: 404-14, 1998). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll, *DNA Cell. Biol.*, 12: 441-53, 1993.

"Polypeptide" and "protein" as used herein, refer to amino acids joined to each other by peptide bonds or modified peptide bonds, i.e., peptide isosteres, and can contain modified amino acids other than the 20 gene-encoded amino acids. The term "polypeptide" also includes peptides and polypeptide fragments, motifs and the like. The term also includes glycosylated polypeptides. The modified host defense peptide, e.g., a D-amino acid modified and/or a retro-inverted host defense peptide, in embodiments of the invention also include all "mimetic" and "peptidomimetic" forms, as described in further detail, below.

"Isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, embodiments of the invention provide nucleic acids which have been purified from genomic DNA or from other sequences in a library or other environment by at least one, two, three, four, five or more orders of magnitude.

Therapeutic Applications

The modified host defense peptide, e.g., a D-amino acid modified and/or a retro-inverted host defense peptide, identified by the methods as described herein can be used in a variety of methods of treatment of infectious disease or inflammatory disease. Thus, the present invention provides compositions and methods for treating an infectious disease, or inflammatory disease. The composition that includes a retroinverted host defense peptide (RI-HDP) and a pharmaceutically acceptable carrier can be used as an adjuvant. The RI-HDP/adjuvant can be administered alone or in combination with an antigenic polypeptides of viral, bacterial, fungal, or parasite origin.

A modified host defense peptide, e.g., a D-amino acid modified and/or a retro-inverted host defense peptide, as described herein, can be used to treat or detect infectious agents including, but are not limited to, bacterial, viral, fungal, or parasitic infectious agents. The modified host defense peptide as provided herein can be used to prevent or treat infectious agents. For example, by increasing the immune response, particularly increasing an innate immune response or increasing the proliferation and differentiation of B and/or T cells, infectious diseases can be treated. The immune response can be increased by either enhancing an existing immune response, or by initiating a new immune response. Alternatively, the modified host defense peptide as provided herein can also directly inhibit the infectious agent, without necessarily eliciting an immune response.

Similarly, bacterial or fungal agents that can cause disease or symptoms and that can be prevented or treated by a modified host defense peptide, e.g., a D-amino acid modified and/or a retro-inverted host defense peptide, include, but not limited to, the following Gram-negative and Gram-positive bacterial families and fungi: *Actinomycetales* (e.g., *Corynebacterium, Mycobacterium, Norcardia*), *Aspergillosis, Bacillaceae* (e.g., *Anthrax, Clostridium*), *Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae* (*Klebsiella, Salmonella, Serratia, Yersinia*), *Erysipelothrix, Helicobacter, Legionellosis, Leptospirosis, Listeria, Mycoplasmatales, Neisseriaceae* (e.g., *Acinetobacter, Gonorrhea, Menigococcal*), *Pasteurellacea Infections* (e.g., *Actinobacillus, Heamophilus, Pasteurella*), *Pseudomonas, Rickettsiaceae, Chlamydiaceae, Syphilis*, and *Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, *dermatocycoses*), toxemia, urinary tract infections, wound infections. A modified host defense peptide, e.g., a D-amino acid modified and/or a retro-inverted host defense peptide, can be used to treat any of these symptoms or diseases.

Bacteremia can be caused by Gram-negative or Gram-positive bacteria. Gram-negative bacteria have thin walled cell membranes consisting of a single layer of peptidoglycan and an outer layer of lipopolysacchacide, lipoprotein, and phospholipid. Exemplary gram-negative organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriacea include, but are not limited to, *Pseudomonas aeruginosa, Stenotrophomonas maltophilia, Burkholderia, Cepacia, Gardenerella, Vaginalis*, and *Acinetobacter* species. Exemplary Gram-negative bacterial species include, but are not limited to, *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis*, or *Salmonella typhi*.

Gram-positive bacteria have a thick cell membrane consisting of multiple layers of peptidoglycan and an outside layer of teichoic acid. Exemplary Gram-positive bacterial targets include, but are not limited to, *Bacillus, Listeria, Sta-*

*phylococcus, Streptococcus, Enterococcus, Clostridium, Mycoplasma, Streptococcus pyogenes, Staphylococcus aureus, Mycobacterium tuberculosis, Streptococcus pneumoniae* coagulase-negative *staphylococci, enterococci*, or *corynebacteria*. Any of the methods and compositions described above are useful for the treatment of skin infections, community-acquired pneumonia, upper and lower respiratory tract infections, skin and soft tissue infections, hospital-acquired lung infections, bone and joint infections, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, central nervous system infections, bacteremia, wound infections, peritonitis, meningitis, infections after burn, urogenital tract infections, gastro-intestinal tract infections, pelvic inflammatory disease, endocarditis, and other intravascular infections. The infections to be treated can be caused by Gram-positive bacteria. These include, without limitation, infections by, *Staphylococcus aureus, Staphylococcus epidermidis, Enterococcus faecalis, Enterococcus faecium, Bacillus subtilis Clostridium perfringens, Clostridium difficile, Streptococcus pyogenes, Streptococcus pneumoniae*, other *Streptococcus* spp., and other *Clostridium* spp. More specifically, the infections can be caused by a Gram-positive coccus, or by a drug-resistant Gram-positive coccus. Exemplary Gram-positive cocci are, without limitation, *S. aureus, S. epidermidis, S. pneumoniae, S. pyogenes, M. catarrhalis, C. difficile, H. pylori, Chlamydia* spp., and *Enterococcus* spp.

Viruses are one example of an infectious agent that can cause disease or symptoms that can be treated or detected by a modified host defense peptide, e.g., a D-amino acid modified and/or a retro-inverted host defense peptide, as provided herein. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiolitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Parasitic agents causing disease or symptoms that can be treated by a modified host defense peptide, e.g., a D-amino acid modified and/or a retro-inverted host defense peptide, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A modified host defense peptide, e.g., a D-amino acid modified and/or a retro-inverted host defense peptide can be used to treat any of these symptoms or diseases.

The compositions and methods described herein are useful for the prevention, treatment or amelioration of inflammatory disease including, but are not limited to, asthma, encephilitis, inflammatory bowel disease (e.g., Crohn's disease and ulcerative colitis), chronic obstructive pulmonary disease (COPD), inflammatory osteolysis, allergic disorders, septic shock, pulmonary fibrosis (e.g., idiopathic pulmonary fibrosis), inflammatory vaculitides (e.g., polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentitated spondyloarthropathy, undifferentiated arthropathy, arthritis, inflammatory osteolysis, chronic hepatitis, and chronic inflammation resulting from chronic viral or bacteria infections. In particular, the composition and methods described herein are useful for the prevention, treatment or amelioration of inflammatory disorders characterized by increased T cell activation and/or abnormal antigen presentation. The compositions and methods described herein can also be applied to the prevention, treatment or amelioration of one or more symptoms associated with inflammatory osteolysis, other disorders characterized by abnormal bone reabsorption, or disorder characterized by bone loss (e.g., osteoporosis).

Similarly, bacterial or fungal agents that can cause disease or symptoms and that can be treated or detected by a polypeptide of the present invention include, but not limited to, the following Gram-Negative and Gram-positive bacterial families and fingi: *Actinomycetales* (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia,* Brucellosis, Candidiasis, *Campylobacter,* Coccidioidomycosis, Cryptococcosis, Dermatocycoses, Enterobacteriaceae (*Klebsiella, Salmonella, Serratia, Yersinia*), *Erysipelothrix, Helicobacter,* Legionellosis, Leptospirosis, *Listeria, Mycoplasmatales,* Neisseriaceae (e.g., *Acinetobacter, Gonorrhea, Menigococcal*), Pasteurellacea Infections (e.g., *Actinobacillus, Heamophilus, Pasteurella*), *Pseudomonas,* Rickettsiaceae, Chlamydiaceae, *Syphilis,* and *Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, *dermatocycoses*), toxemia, urinary tract infections, wound infections. A polypeptide or polynucleotide of the present invention can be used to treat or detect any of these symptoms or diseases.

Preferably, treatment using modified host defense peptide, e.g., RI-BMAP-28, in an embodiment of the present invention could either be by administering an effective amount of the a modified host defense peptide, e.g., a D-amino acid modified and/or a retro-inverted host defense peptide, to the patient. Moreover, the polypeptide or peptidomimetic as provided herein can be used to reduce or eliminate bacterial, viral, fungal, or parasitic infectious disease or inflammatory disease.

Pharmaceutical Compositions

A modified host defense peptide, e.g., a D-amino acid modified and/or a retro-inverted host defense peptide, useful in the present compositions and methods can be administered to a human patient per se, in the form of a stereoisomer, prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount, for example, to treat bacterial, viral, fungal, or parasitic infectious disease or inflammatory disease.

"Therapeutically effective amount" refers to that amount of the therapeutic agent, a modified host defense peptide, e.g., a D-amino acid modified and/or a retro-inverted host defense peptide, sufficient to result in the amelioration of one or more symptoms of a disorder, or prevent advancement of a disorder, cause regression of the disorder, or to enhance or improve the therapeutic effect(s) of another therapeutic agent. With respect to the treatment of infectious diseases, a therapeutically effective amount refers to the amount of a therapeutic agent sufficient to reduce or inhibit the replication of an infectious agent (e.g., bacteria or fungi), kill the infectious agent, inhibit or reduce the spread of the infectious agent to other tissues or subjects, or ameliorate one or more symptoms associated with the infectious disease. Preferably, a therapeutically effective amount of a therapeutic agent reduces the replication or spread of an infectious agent by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. With respect to the treatment of an inflammatory disorder or an autoimmune disorder characterized by inflammation, a therapeutically effective amount refers to the amount of a therapeutic agent that reduces the inflammation of a joint, organ or tissue by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. "Therapeutic protocol" refers to a regimen for dosing and timing the administration of one or more therapeutic agents, such as a modified host defense peptide, e.g., a D-amino acid modified and/or a retro-inverted host defense peptide.

Pharmaceutically acceptable carriers are determined in part by the particular composition being administered, as well as by the particular method used to administer the composition. Accordingly, there is a wide variety of suitable formulations of pharmaceutical compositions for administering the antibody compositions (see, e.g., Remington's Pharmaceutical Sciences, Mack Publishing Co., Easton, Pa. 18$^{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Labels

The particular label or detectable group used in the assay is not a critical aspect of the invention, so long as it does not significantly interfere with the specific binding of the modified host defense peptide, e.g., a D-amino acid modified and/or a retro-inverted host defense peptide, used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^{3}$H, $^{14}$C, $^{35}$S, $^{125}$I, $^{121}$I, $^{112}$In, $^{99}$mTc), other imaging agents such as microbubbles (for ultrasound imaging), $^{18}$F, $^{11}$C, $^{15}$O, (for Positron emission tomography), $^{99}$mTC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems which can be used, see, U.S. Pat. No. 4,391,904, incorporated herein by reference in its entirety and for all purposes.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple calorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Frequently, the modified host defense peptide, e.g., a D-amino acid modified and/or a retro-inverted host defense peptide, will be labeled by joining, either covalently or non-covalently, a substance which provides for a detectable signal.

Treatment Regimes

Embodiments of the invention provide pharmaceutical compositions comprising one or a combination of modified host defense peptides, e.g., a D-amino acid modified and/or a retro-inverted host defense peptide, formulated together with a pharmaceutically acceptable carrier. Some compositions include a combination of multiple (e.g., two or more) modified host defense peptides, e.g., RI-BMAP-28. The composition that includes a retroinverted host defense peptide (RI-HDP) and a pharmaceutically acceptable carrier can be used as an adjuvant.

In prophylactic applications, pharmaceutical compositions or medicaments are administered to a patient susceptible to, or otherwise at risk of a disease or condition (i.e., bacterial, viral, fungal, or parasitic infectious disease or inflammatory disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

The composition that includes a retroinverted host defense peptide (RI-HDP) and a pharmaceutically acceptable carrier can be used as an adjuvant. The RI-HDP/adjuvant can be administered alone or in combination with an antigenic polypeptides of viral, bacterial, fungal, or parasite origin. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. The pharmaceutical composition of a retroinverted host defense peptide as described herein will have immunoregulatory activity. The RI-HDP composition can be used as an adjuvant that directly acts as a T and/or B cell activator or acts on specific cell types that enhance the synthesis of various cytokines or activates intracellular signaling pathways. Such RI-HDP polypeptides are expected to augment the immune response to increase the protective index of vaccine compositions that include an antigenic polypeptides or viral, bacterial, fungal, or parasite origin. When used in combination with an antigenic polypeptide, the pharmaceutical composition can contain, for example, the antigenic polypeptide to give a final dose of 50 mg protein in a 0.1 ml injectable volume in combination with an RI-HDP polypeptide adjuvant. The RI-HDP polypeptide adjuvant concentration can be in the range of 0.1 to 10 mg RI-HDP polypeptide per kg body weight of the patient to be treated. The RI-HDP polypeptide adjuvant concentration can further be in a range of 1-10 mg/kg or 0.5 to 5.0 mg/kg, of the patient body weight. On a per vaccine dose basis one can administer from 50 to 500 µg of RI-HDP polypeptide adjuvant per vaccine formulation that would be delivered as a single unit independent of the weight of the patient.

Effective Dosages

Effective doses of the modified host defense peptide, e.g., a D-amino acid modified and/or a retro-inverted host defense peptide, for the treatment of bacterial, viral, fungal, or parasitic infectious disease or inflammatory disease as described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with a modified host defense peptide, e.g., a D-amino acid modified and/or a retro-inverted host defense peptide, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or a modified host defense peptides, e.g., a D-amino acid modified and/or a retro-inverted host defense peptide with different binding specificities are administered simultaneously, in which case the dosage of each retro-inverted host defense peptide is usually administered on multiple occasions. Intervals between single dosages can be weekly, monthly or yearly. Intervals can also be irregular as indicated by measuring blood levels of retro-inverted host defense peptide in the patient. In some methods, dosage is adjusted to achieve an antibody concentration of 1-1000 µg/ml and in some methods 25-300 µg/ml. Alternatively, antibody can be administered as a sustained release formulation, in which case less frequent administration is required. Dosage and frequency vary depending on the half-life of the compound in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of bacterial, viral, fungal, or parasitic infectious disease or inflammatory disease. Thereafter, the patent can be administered a prophylactic regime.

Doses for a modified host defense peptide, e.g., a D-amino acid modified and/or a retro-inverted host defense peptide, range from about 10 ng to 1 g, 100 ng to 100 mg, 1 µg to 10 mg, or 30-300 µg DNA per patient. Doses for infectious viral vectors vary from 10-100, or more, virions per dose.

Prodrugs

The present invention is also related to prodrugs of the agents obtained by the methods disclosed herein. Prodrugs are agents which are converted in vivo to active forms (see, e.g., R. B. Silverman, 1992, *The Organic Chemistry of Drug Design and Drug Action*, Academic Press, Chp. 8). Prodrugs can be used to alter the biodistribution (e.g., to allow agents which would not typically enter the reactive site of the protease) or the pharmacokinetics for a particular agent. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate agent which subsequently decomposes to yield the active agent. The prodrug moieties can be metabolized in vivo by esterases or by other mechanisms to carboxylic acids.

Examples of prodrugs and their uses are well known in the art (see, e.g., Berge et al., "Pharmaceutical Salts", *J. Pharm. Sci.* 66: 1-19, 1977). The prodrugs can be prepared in situ during the final isolation and purification of the agents, or by separately reacting the purified agent in its free acid form with a suitable derivatizing agent. Carboxylic acids can be converted into esters via treatment with an alcohol in the presence of a catalyst.

Examples of cleavable carboxylic acid prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides.

Routes of Administration

A modified host defense peptide, e.g., a D-amino acid modified and/or a retro-inverted host defense peptide for treatment or amelioration of bacterial, viral, fungal, or parasitic infectious disease or inflammatory disease can be administered by parenteral, topical, intravenous, oral, subcutaneous, intraarterial, intracranial, intraperitoneal, intranasal or intramuscular means for prophylactic as inhalants for modified host defense peptide, e.g., a D-amino acid modified and/or a retro-inverted host defense peptide preparations targeting bacterial, viral, fungal, or parasitic infectious disease or inflammatory disease, and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where a tumor is found, for example intracranial injection or convection enhanced delivery. Intramuscular injection or intravenous infusion are preferred for administration of antibody. In some methods, particular therapeutic antibodies are delivered directly into the cranium. In some methods, antibodies are administered as a sustained release composition or device, such as a Medipad™ device.

Agents of the invention can optionally be administered in combination with other agents that are at least partly effective in treating various diseases including bacterial, viral, fungal, or parasitic infectious disease or inflammatory disease. In the case of infection in the brain, agents of the invention can also be administered in conjunction with other agents that increase passage of the agents of the invention across the blood-brain barrier (BBB).

Formulation

A modified host defense peptide, e.g., a D-amino acid modified and/or a retro-inverted host defense peptide, for the treatment of bacterial, viral, fungal, or parasitic infectious disease or inflammatory disease, are often administered as pharmaceutical compositions comprising an active therapeutic agent, i.e., and a variety of other pharmaceutically acceptable components. See Remington's Pharmaceutical Science (15$^{th}$ ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of embodiments of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., *Nature* 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Toxicity

Preferably, a therapeutically effective dose of the modified host defense peptide, e.g., a D-amino acid modified and/or a retro-inverted host defense peptide, described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the modified host defense peptide, e.g., a D-amino acid modified and/or a retro-inverted host defense peptide of embodiments of the invention and instructions for use. The kit can further contain a least one additional reagent, or one or more additional human antibodies of embodiments of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

The invention will be further described with reference to the following examples; however, it is to be understood that the invention is not limited to such examples.

EXEMPLARY EMBODIMENTS

Example 1

Predicted Topology of BMAP-28 and RI-BMAP-28

As peptides are directional and chiral molecules there is the potential to modify each of these parameters, individually or in combination, to create novel peptides with improved pharmacological properties. Retro-peptides are direction isomers in which the sequence of the peptide is reversed with respect to the parent peptide. Inverso-peptides share the same sequence as the parent peptide but with inverted stereochemistry at the alpha carbon chiral centers i.e. D-amino acids. Retroinverso peptides incorporate both of these modifications with reversal of sequence and utilization of D-amino acids. As such, the parent peptide is composed of L-amino acids in the sequence order (1, 2, 3, n) where residue 1 occupies the amino terminal position of the peptide. The corresponding retroinversed peptide is composed of D-amino acids in the sequence order (m, 3, 2, 1) where residue 1 now occupies the carboxy terminal position [FIG. 1A]. When the retroinversed peptide is rotated by 180 degrees in the plane of the diagram the sequence of the modified peptide now reads (1, 2, 3, n) and the side chains superimpose in three-dimensional space with those of the parent peptide. RI peptides are therefore derivatives of natural peptides in which the relative side chain toplogy is maintained while the backbone termini and direction of the peptide bonds is reversed i.e. (—NH—CO—) versus (—CO—NH—) [FIG. 1B].

FIG. 1 shows structure and sequence of peptides and the retroinversed counterparts. A) Sequence of BMAP-28 and RI-BMAP-28. B) Retro-inverso peptides present the same three dimensional structures with respect to side chains but have a reversal of the peptide bonds.

Example 2

RI-BMAP-28 is Resistant to Proteolytic Degradation

There is a physiological requirement for the turnover of cellular proteins as well as the digestion of consumed proteins. This is achieved largely through the action of proteolytic enzymes which recognize particular sub-groups of amino acids within the context of peptides or proteins and hydrolyse the adjacent peptide bond. Peptide bonds involving D-amino acids, as in RI-peptides, are resistant to this cleavage as the majority of proteolytic enzymes are incapable of attacking these linkages, Fauchere et al., *Adv. Drug. Res.* 23: 127-159, 1992.

To quantify the extent to which retroinversion protects BMAP-28 from proteolytic degradation BMAP-28 and RI-BMAP-28 were incubated in an excess of trypsin and the extent of their digestion determined at a variety of time points. Trypsin was selected as a representative serine protease as both BMAP-28 and RI-BMAP-28, which share an identical amino acid composition, are rich in lysine and arginine residues, 7 out of 27 residues, and therefore should represent strong potential substrates for this enzyme. Under the digestion conditions employed all of the molecules of BMAP-28 were cleaved at least once by trypsin within a 30 minute time period. In contrast, RI-BMAP-28 remained completely intact even after eight hours of digestion [FIG. 2].

FIG. 2 shows RI-BMAP-28 is Resistant to Proteolytic Degradation. BMAP-28 and RI-BMAP-28 (1 mg/mL) were digested with trypsin (0.1 mg/ml) in a 50 µL reaction volume (50 mM Tris pH 7.2) at 37° C. Digestion mixtures were then separated via HPLC chromatography and the extent of peptide degradation quantified through comparison of peak areas to that of an undigested sample of the same peptide.

Example 3

BMAP-28 and RI-BMAP-28 Adopt Similar Conformations

Retroinversed peptides are predicted to present the same topology of side chains as their natural counterparts when in an extended conformation. However caution must be exerted in assuming that either directional (retro) or retroinverso peptides will adopt identical higher order structures as their parent peptides, Fischer, *Curr. Prot. and Pept. Sci.* 4: 339-356, 2003.

For example, natural peptides in α-helical conformation present a right-handed helix. An enantiomeric derivative of the same peptide, i.e. all D-amino acids, will also form a helical structure but of a left-handed nature and the circular dichroism spectra of these two peptides will be mirror images of each other. However with retroinversed peptides alterations to main chain hydrogen bonding patterns, as well as dipole moments which are dependent upon the direction of hydrogen bonds, can favor an alternate structures than those preferred by the natural peptide. Having said that examples of peptides and their RI-counterparts which adopt identical higher-order conformations have been reported, Merrifield et al., *Proc. Natl. Acad. Sci. USA* 88: 4240-4244, 1995.

Circular dichroism was employed to identify and quantify elements of secondary structure within BMAP-28 and RI-BMAP-28. As has been observed for other cathelicidin HDPs both BMAP-28 and RI-BMAP-28 assume random structures in aqueous solution [data not shown]. For many cathelicidins the formation of defined secondary structure is induced upon contact with hydrophobic membranes, Merrifield et al., *Proc. Natl. Acad. Sci. USA* 88: 4240-4244, 1995, Skerlavaj et al., *J. Biol. Chem.* 271: 28375-28381, 1996. For CD investigations this can be experimentally mimicked with the addition of TFE to the reaction solutions, Skerlavaj et al., *J. Biol. Chem.* 271: 28375-28381, 1996. Under these conditions both BMAP-28 and RI-BMAP-28 adopted defined structures whose spectrums are mirror images of each other indicating the formation of symmetrically related structures. [FIG. 3*a*].

Deconvolution of the CD spectra to determine the relative compositions of the different elements of secondary structure within each peptide verified the formation of identical patterns of higher-order structure within the two molecules [FIG. 3*b*]. The calculated percentage compositions are also relatively consistent with what has been reported by others for BMAP-28 (30). The structures of cathelicidins such as BMAP-28 have been shown to be dynamic and highly sensitive to experiment conditions, it is most pertinent that under identical experimental conditions BMAP-28 and RI-BMAP-28 form highly comparable structures.

FIG. 3 shows RI-BMAP-28 Adopts a Similar Three Dimensional Conformation as BMAP-28. A) CD Spectra of BAMP28 and RI-BMAP-28. B) Percentage Composition of Different Elements of Secondary Structure.

Example 4

RI-BMAP-28 has Improved Direct Antimicrobial Activity

Others have examined the functional consequences of D-amino acid substitutions as well as partial retro-inversion of HDPs on direct antimicrobial activity, Merrifield et al., *Proc. Natl. Acad. Sci. USA* 88: 4240-4244, 1995. These investigations have reported either maintained or improved direct antimicrobial activity. These investigations have also reported changes in direct antimicrobial efficiency which are dependent upon the particular strain of bacteria suggesting the involvement of specific interactions and mechanisms of action rather than non discriminating disruption of membranes.

Figure 4:
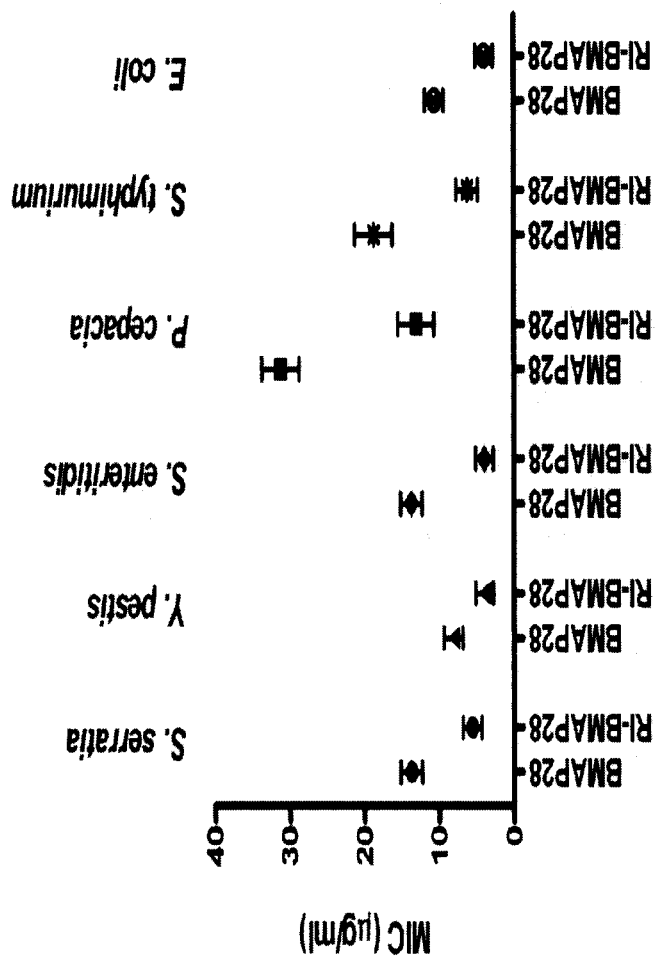
FIG. 4 shows minimum inhibitory concentrations of BMAP-28 and RI-BMAP-28.

The present study examined the direct antimicrobial activity of BMAP-28 and RI-BMAP-28 against a series of bacterium which are of medical interest. Against all the strains tested, RI-BMAP-28 demonstrated a consistent improvement in direct antimicrobial activity. The MICs values for the RI-BMAP-28 were typically half to a third of that of the natural peptide (FIG. 4). The present study did not observe any strain specificity to the improved activity of RI-MAP-28 with any of the bacteria that were examined. That RI-BMAP-28 showed a consistent and conserved improvement against all of the bacteria examined suggests that the improvement reflects alteration of a general characteristic of the peptide, such as biological stability rather than an alteration to the mechanism by which it mediates bacterial killing. This conclusion is also consistent with the maintained sequence and structure of the RI-BMAP-28. Antimicrobial activity, which is dependent upon non-chiral interactions with bacterial membranes, is anticipated to have the lowest structural requirements for maintenance of activity.

FIG. 4 shows minimum inhibitory concentrations of BMAP-28 and RI-BMAP-28: The MIC values represent the averages of triplicate experiments.

Example 5

RI-BMAP-28 is an Equally Effective PhoQ Ligand

Biological mechanisms which are dependent upon interactions with protein effectors are anticipated to present more stringent structural requirements for the maintenance of activity. However, the precise requirements will depend on whether the interactions are dominated by electrostatic interactions involving side chains or hydrogen bonding interactions with the main-chain of the peptide. Both types of interactions with proteins are believed to be of physiological significance to HDPs.

With respect to interactions with proteins that are determined predominately by electrostatic interactions, host defense peptides have been shown to serve as ligands for the bacterial two-component sensory protein PhoQ. In response to host defense peptides or $Mg^{2+}$ depleted conditions, this histidine kinase, through activation of the cognate response regulator PhoP, initiates patterns of gene expression associated with both bacterial virulence and adaptive responses, including membrane modifications that bestow HDP resistance, Bader et al., *Cell* 122: 461-472, 2005. This interaction has been proposed to function largely through electrostatic interactions between the cationic HDPs and an acidic surface of PhoQ. While no structural information is yet available for complexes of PhoQ with peptide ligands, the peptide binding region has been predicted, and verified, through a variety of experimental approaches, Bader et al., Cell 122: 461-472, 2005; Cho et al., J. Mol. Biol. 5: 1193-1206, 2006. In the proposed model, a planar acidic surface of PhoQ runs parallel to the bacterial membrane. Electrostatic repulsion between the negatively charged bacterial membrane and the acidic surface of PhoQ is neutralized by the coordination of cations by metal binding sites of PhoQ. These electrostatic bridges dock the sensory domain to the membrane in an inactive conformation. In the absence of these counterions, electrostatic repulsion displaces the sensory domain from the membrane resulting in activation of the protein. Similarly, the binding of HDPs to PhoQ causes similar displacement resulting in activation of the system. In the crystallographic structure, this region was found to coordinate calcium ions and is suggested by a variety of techniques to represent the region of the protein responsible for binding both metal ions as well as cationic peptides Cho et al., J. Mol. Biol. 5: 1193-1206, 2006.

The ability of HDP and RI-HDPs to serve as ligands for PhoQ system is an interesting test of ligand specificity. The association of HDPs with the protein requires the interaction between two chiral molecules, yet the interaction is predicted to be dictated predominantly by the charged side chains of the protein and peptide and therefore should be largely independent of changes to the main-chain hydrogen-bonding characteristic of the RI-peptide.

S. typhimurium strain CS 120, which expresses a PhoP-regulated fusion between Salmonella acid phosphatase (PhoN) and E. coli alkaline phosphatase (PhoA), was utilized for the analysis of PhoPQ activation. The activity of this fusion protein was measured in media containing varying concentrations of the peptides and/or magnesium. For growth under PhoPQ activating conditions the growth media was supplemented with 50 µM MgCl2. Growth under PhoPQ-repressive conditions was performed in the presence of 5 mM MgCl2 as were all of the assays of peptide responses.

Retroinversion of BMAP-28 did not influence its ability to function as a PhoQ ligand. Both BMAP-28 and RI-BMAP-28 achieved identical patterns of activation of the reporter indicating that the natural and modified peptides were equally potent ligands for PhoQ [FIG. 5]. As there is considerable interest in understanding how this bacterial sensory protein is able to detect and respond to a wide range of host defense peptides it is of value in determining that these receptor-ligand interactions are determined primarily through elctrostatic interactions via the side chain residues. This also indicates that retroinversion is not likely an effective strategy for therapeutic HDPs to circumvent activation of this system and subsequent induction of undesired bacterial offensive and defensive strategies.

Figure 5:
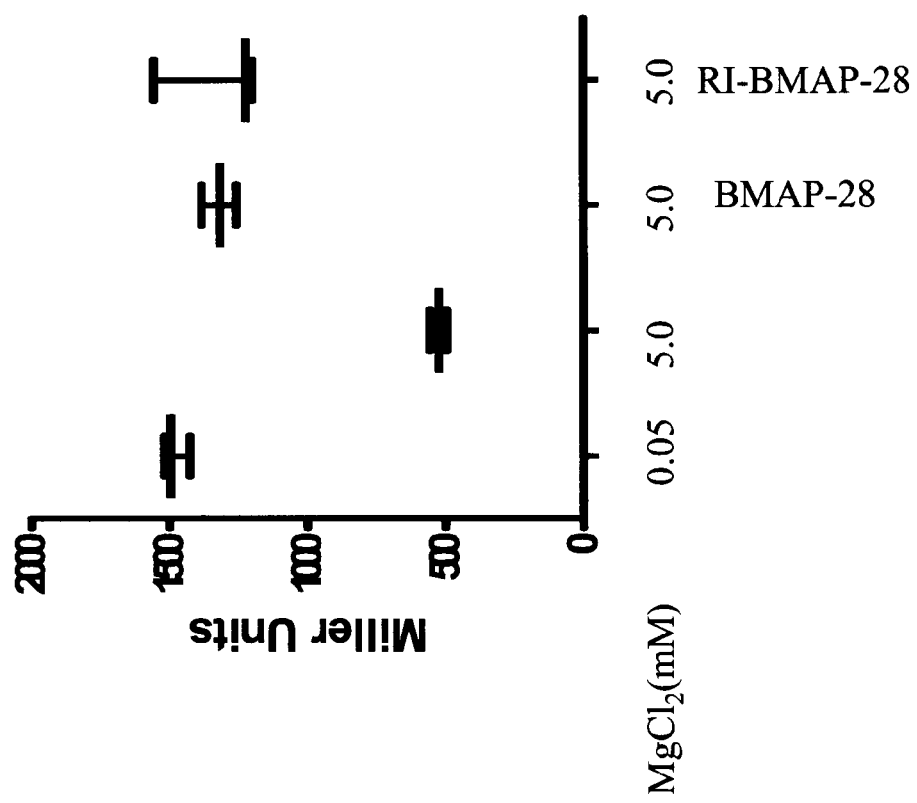
FIG. 5 shows activation of PhoPQ by BMAP28 and RI-BMAP28.

FIG. 5 shows activation of PhoPQ by BMAP28 and RI-BMAP28. The ability of BMAP28 and RI-BMAP28 to initiate activation of a PhoPQ-dependent reporter was examined by incubation of bacterium in the presence of sub-lethal (5 µg/mL) concentrations of indicated peptide as well as 5 mM magnesium. Values reported represent the averages of three replicates. Activation and repression of PhoPQ by low (50 µM) and high (5 mM) magnesium respectively is also reported.

Example 6

HDPs Modulate Inflammation Responses

The medical risks associated with bacterial infection involve both the direct pathogenic mechanisms of the microbe as well as the potential for self-induced pathology as a consequence of excessive inflammatory responses. While conventional antibiotics are able to neutralize bacteria they are unable to address issues relating to inflammation. In contrast, while many of the biological actions initiated by HDPs, such as promoting the release of cytokines, chemokines and histamine, are proinflammatory these peptides also appear to function to modulate the potentially deleterious consequences of inflammation. This is highly significant as excessive inflammatory responses in the form of sepsis are responsible for approximately 200,000 deaths per year, Angus et al., Crit. Care Med 29: 1303-10, 2001.

Previous studies have suggested that the anti-endotoxic activity of cationic peptides results in part from LPS chelation, Scott, et al., J. Immunol. 164: 549-553, 2000. Evidence has been presented however to indicate that the suppression of LPS-induced, pro-inflammatory responses by HDPs involves mechanisms independent of LPS chelation. Notable that HDPs are able to influence inflammatory responses even when applied to cells following a sufficient duration for LPS uptake, Mookherjee et al., J. Leokocyte. Biol. 80:1-12, 2006, and that HDPs also modulate cellular responses initiated by activation of other Toll-like receptors such as TLR2 and TLR9, Mookherjee et al., J. Immunol. 176: 2455-2464, 2006.

While the specific details have yet to be elucidated it appears that host defense peptides modulate inflammation responses by functioning as signaling molecules. There have been numerous reports of HDPs binding to a variety of receptors, Tjabring a et al., J. Immunol. 171: 6690-6696, 2003; Yang et al., J. Exp. Med. 192: 1069-1074, 2000; Niyonsaba et al., Int. Immunol. 14: 421-426, 2002; Elssner et al., J. Immunol. 172: 4987-4994, 2004, to the activation of specific signal transduction pathways and mobilization of $Ca^{2+}$ stores, Tjabring a et al., J. Immunol. 171: 6690-6696, 2003; Niyonsaba et al., Int. Immunol. 14: 421-426, 2002; Lau et al., Infect. Immun. 73: 583-591, 2005; Bowdish et al., J. Immunol. 172: 3758-3765, 2004. For example, LL-37, the sole human cathelicidin, mediates chemotaxis of neutrophils, monocytes and T cells through formyl peptide receptor-like 1, Kurasaka et al., J. Immunol. 174: 6257-6265, 2005. Retention of activities that require interaction with specific protein receptors would be anticipated to be the most stringent test for the retroinversed HDPs.

Example 7

RI-BMAP-28 Suppresses LPS-Induced Patterns of Gene Expression

The induction of inflammation responses by lipopolysaccharide (LPS) has clinical significance as a mechanism of sepsis and also serves as a biomarker for the ability of HDPs to mediate anti-endotoxic function. Our investigation focuses on patterns of expression of genes (BIRC3, CCL20, IL-8 and IL-10) identified through microarray analysis to show the most significant levels of differential expression in response to LPS-stimulation in monocytes, Mookherjee et al., J. Leokocyte. Biol. 80:1-12, 2006; Mookherjee et al., J. Immunol. 176: 2455-2464, 2006. Under LPS-stimulation the induction of these genes has also been shown to be modulated by HDPs, Mookherjee et al., J. Leokocyte. Biol. 80:1-12, 2006; Mookherjee et al., J. Immunol. 176: 2455-2464, 2006.

Both BMAP-28 and RI-BMAP-28 mediate an identical pattern of suppression of genes which are induced by LPS-stimulation. This suppression is mediated in a dose dependent fashion with 5 µg/mL of either the natural or retroinversed peptide resulting in four to five-fold suppression of the induction achieved via stimulation with 100 ng of LPS. Even at the lowest concentration tested of 0.5 µg/mL both peptides were able to achieve significant repression of the genes examined, a two-fold reduction for both IL-10 and CCL20 and four-fold for 11-8 [FIG. 6]. While the physiological concentrations of BMAP-28 have not been determined, it has been demonstrated that other cathelicidins are present at concentrations in the range of 2 to 20 µg/ml, Bowdish et al., *J. Immunol.* 172: 3758-3765, 2004.

Figure 6:
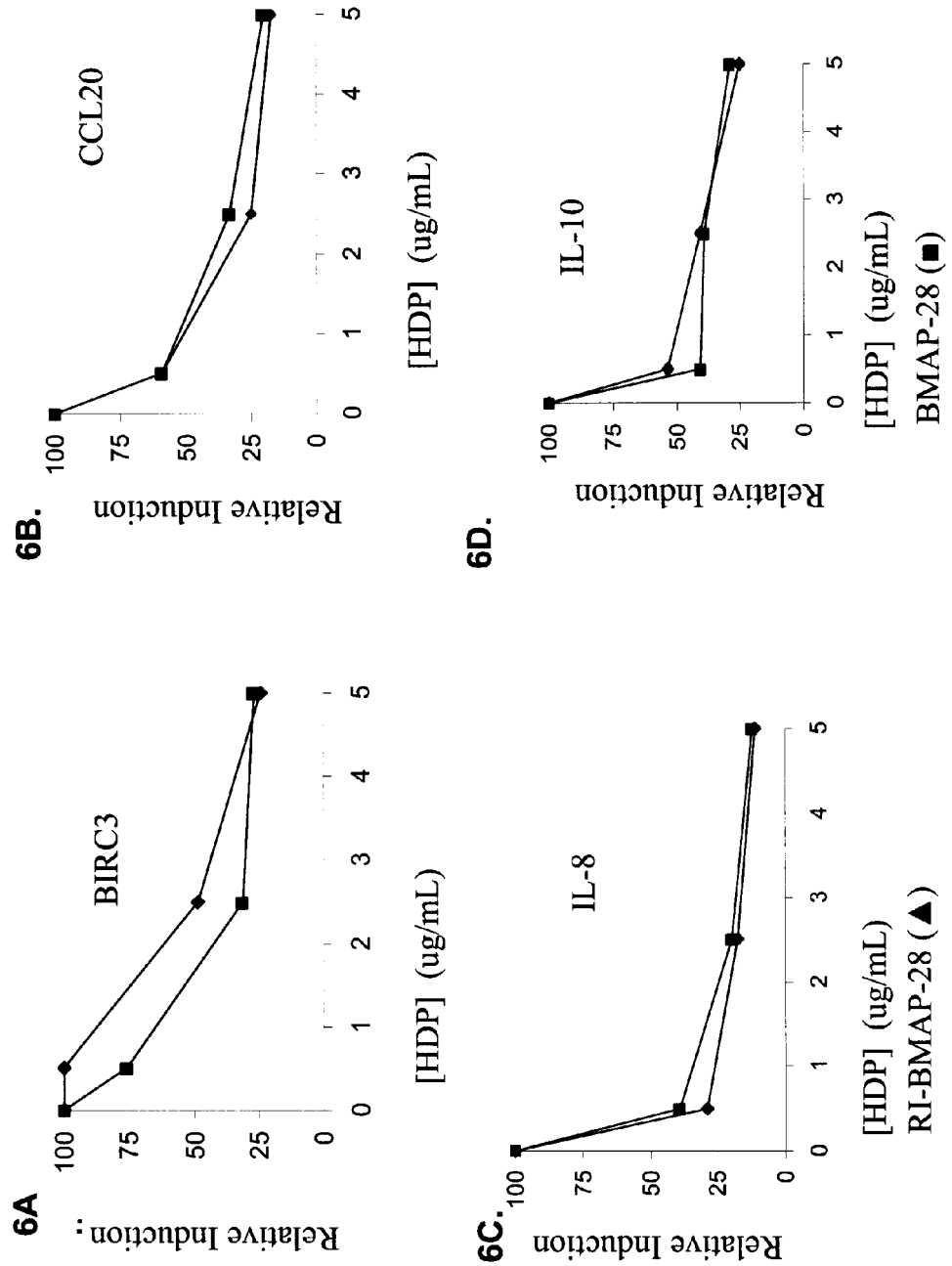
FIG. 6 shows HDP inhibition of LPS-induced gene expression.

FIG. 6 shows HDP Inhibition of LPS-Induced Gene Expression: Bovine monocytes ($5 \times 10^5$ cells/well) were stimulated with 100 ng/ml of LPS (*E. coli*) in the presence and absence of HDPs. The data presented represents the average of experiments performed in triplicate for a single animal. While all three animals, each tested in triplicate, gave the same trend of responses, the magnitude of these responses is unique for each animal. This is typical of the animal-to-animal variation in the magnitude of LPS-induced responses that has been observed by our group.

Example 8

RI-BMAP-28 Equally Suppresses LPS-Induced TNF-α Release

As patterns expression are not necessarily predictive of final biological responses we sought to confirm the immunomodulatory capabilities of RI-BMAP-28 through independent analysis. Specifically, the ability of the two isomers to influence secretion of the pro-inflammatory cytokine tumor necrosis factor alpha (TNF-α) following LPS stimulation was examined. Secretion of TNF-α is a well established biomarker of inflammation responses (52).

Results of ELISA assays confirmed the abilities for both BMAP-28 and R1-BAMP28 to effectively suppress LPS-induced TNF-α secretion. Similar dose-dependent inhibition of LPS-induced TNF-α was observed with BMAP-28 and RI-BMAP-28 in bovine PBMCs. While the exact magnitude of these responses often show significant animal-to-animal variation conservation of trends within cells collected from the different animal was demonstrated. See FIG. 7. In particular within cells collected from the same animal both BMAP-28 and RI-BMAP-28 mediated identical patterns of suppression. Importantly the peptide concentration required to mediate this effect is consistent with that required to influence patterns of gene expression.

Figure 7:
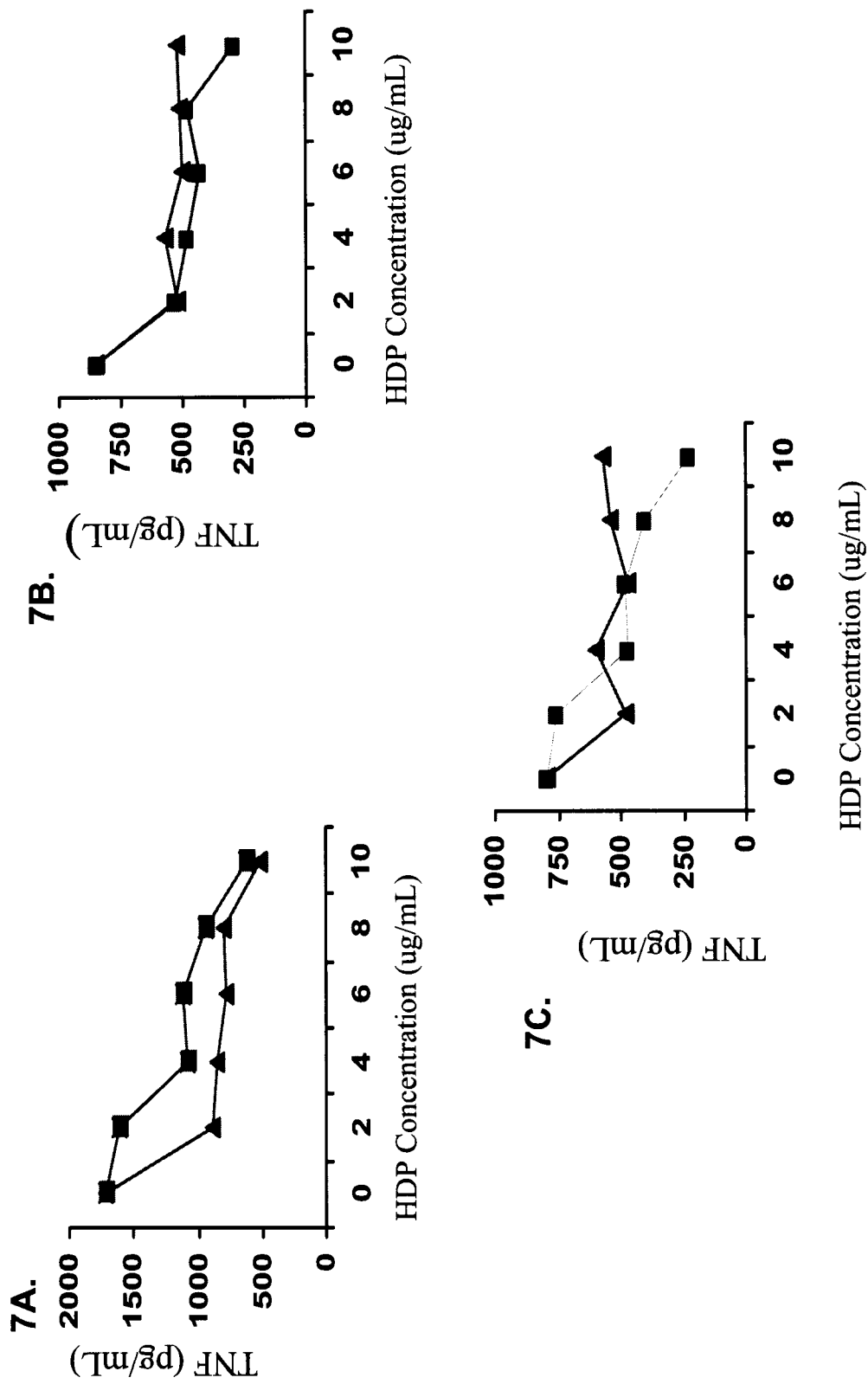
FIG. 7 shows HDP inhibition of LPS-induced TNF secretion.

FIG. 7 shows HDP Inhibition of LPS-Induced TNF Secretion: Bovine PBMCs ($5 \times 10^5$ cells/well) were stimulated with 100 ng/ml of LPS (*E. coli*) for 48 h. The secretion of TNF in culture supernatants was quantified with a capture ELISA. Inhibition of LPS-induced TNF secretion was evaluated by adding various concentrations of BMAP-28 (▲) or retro-inverso RI-BMAP-28 (■) to duplicate PBMCs cultures. The data presented experiments performed in a single animal. While all three animals gave the same trend of responses, the magnitude of these responses is unique for each animal. This is typical of the animal-to-animal variation in the magnitude of LPS-induced responses that has been observed by our group.

Example 9

Host Cell Toxicity

To be considered as a therapeutic agent it is essential that HDPs do not exert host cell toxicity in the range of concentrations that are required to exert a therapeutic effect. As the mechanism of direct antimicrobial activity appears to be principally mediated through relatively non-specific interactions with membranes this does suggest the potential for deleterious interactions with host membranes. While the lack of anionic lipids, the absence of strong membrane potential gradient and the presence of cholesterol make eukaryotic membranes poorer targets for HDPs host toxicity still remains an issue. Efforts have been made to reduce HDP toxicity through manipulations of sequence and properties with moderate success, Chen et al., *J. Biol. Che.* 280: 12316-12329, 2005; Lee et al., *J. Pept. Res.* 63: 69-84, 2004; Oren et al., *Biochem.* 36: 1826-1835, 1997.

In tissue culture BMAP-28 is toxic to mammalian cells at concentrations above 10 µM (30 µg/mL), Giacometti et al., *Crit. Care Med.* 32: 2555-2556, 2004, and in vivo the LD50 values were determined to be approximately 40 mg/kg for mice via i.p. administration. BMAP-28 proved to be more toxic when administered intravenously with LD50 values of 15 mg/kg, Giacometti et al., *Crit. Care Med.* 32: 2555-2556, 2004. From these findings the authors concluded BMAP-28 was not safe for i.v. administration and that the therapeutic potential was restricted to topical treatments, Giacometti et al., *Crit. Care Med.* 32: 2555-2556, 2004. While BMAP-28 is one of the more toxic HDPs these trends are observed for other peptides of the same class. As such toxicity is a critical issue to be addressed before consideration of the systemic administration of these molecules.

To determine the cytotoxicity of BMAP-28 and RI-BMAP-28 the peptides were incubated overnight at a range of concentrations in the presence of bovine erythrocytes. Consistent with what has been reported by others, BMAP-28 began to exert a cytotoxic effect at concentrations as low as 30 µg/mL. Complete hemolysis was observed by 200 µg/mL of BMAP-28. In contrast, RI-BMAP-28 did not exhibit any cytotoxic effects over the range of peptide concentrations examined [FIG. 8]. As toxicity currently represents a limiting factor to the systemic administration of HDPs this finding could be of particular significance.

We do not have a definitive explanation for this unexpected, but highly desirable, outcome of elimination of hemolytic activity through retro-inversion of BMAP-28. We speculate that the toxicity of BMAP-28 can be due to a degradation product rather than the full length molecule and as RI-BMAP-28 is resistant to proteolytic breakdown it does not form the cytotoxic species. Supportive of this hypothesis is the report that the cytotoxicity of BMAP-28 is localized to the hydrophobic C-terminal tail of the peptide, Skerlavaj et al., *J. Biol. Chem.* 271: 28375-28381, 1996. Investigations are underway to test this hypothesis.

Figure 8:
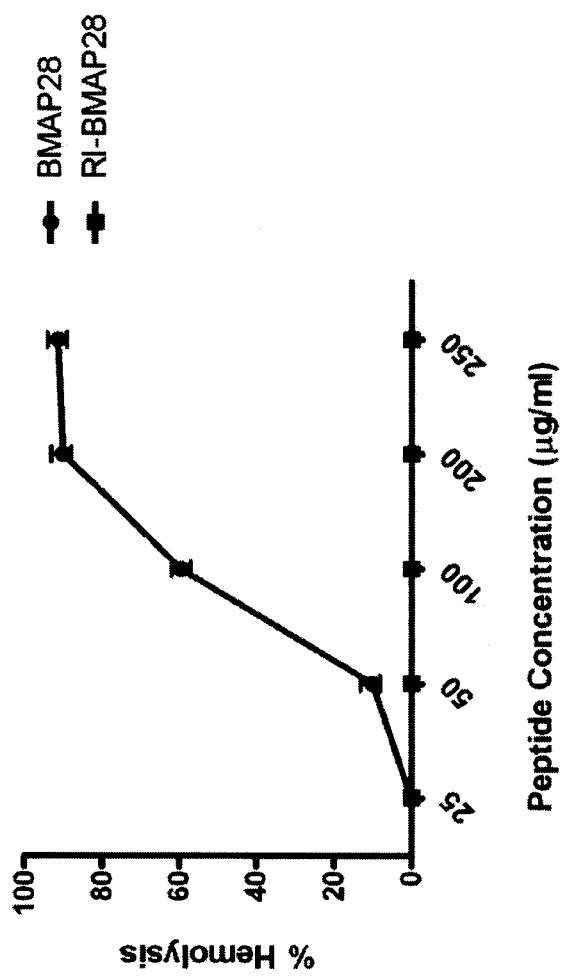
FIG. 8 shows cytotoxicity of BMAP-28 and RI-BMAP-28.

FIG. 8 shows cytotoxicity of BMAP-28 and RI-BMAP-28. Hemolysis was performed by incubating a 1% (v/v) suspension of bovine erythrocytes in phosphate buffered saline (pH 7.4) with a series of peptide concentrations for 12 hours at 37° C. Samples were then centrifuged and the supernatant absorbance read at 415 nm. Total hemolysis was obtained by resuspending in cells in water rather than PBS. Results are the average from four independent experiments.

Example 10

Retro-Inverted Host Defense Peptides Active Innate Immune Response, Modulate Deleterious Inflammation, and Mediate Direct Antimicrobial Activity The ability of HDPs to active innate immune responses, modulate deleterious inflammation and mediate direct antimicrobial activity against a diverse spectrum of bacteria are all highly desirable characteristics for antibiotics. While host defense peptides have proven themselves effective as topical antimicrobials the ability to make the transition into treatments of systemic infections will be dependent upon the ability to address issues relating to toxicity, cost and biological stability. Efforts to transform HDPs into more effective pharmacological agents have focused on three distinct strategies.

Firstly to address issues relating to cost of synthesis successful efforts have been made to develop novel biological production systems such as the fungal-system recently reported for synthesis of the HDP plectasin, Mygind et al., Nature 437: 975-980, 2005. These biological production systems allow researchers to circumvent the costly processes of chemical synthesis. This approach is disadvantaged however by the inability to incorporate non-standard amino acids as well as the need to purify the peptides away from biological contaminants. Secondly, efforts have been made to identify minimal active structures or sequences within the peptides that are responsible for the biological activities. This allows for reduction of the required peptide length. While a valid and rational approach, there is the potential that the structural minimization of these molecules can compromise their full biological potential as different activities can be attributed to different regions of the molecule. Lastly through peptide modifications that stabilize the peptides against biological degradation might reduce both toxicity and cost.

Within this third approach sequence, stereochemical and directional modifications of a native peptides attempt to convert peptides into more pharmaceutically acceptable drugs. These modifications include sequence derivatives, D-amino acids and the use of non-standard peptide backbones to reduce toxicity and improve stability, Hancock et al., Nat. Biotech. 24: 1551-1557, 2006. Creation of antibiotics via non-standard amino acids and linkages is borrowed from nature where microbes often employ non-ribosomal-peptide synthetase complexes to produce peptide-based antibiotics with D-amino acids, non-standard amino acids and unique patterns of modification to evade bacterial defensive and adaptive strategies Finking et al., Annu. Rev. Microbiol. 58: 453-488, 2004.

Retro-inversion has potential to stabilize the peptides while maintaining biological activity. Through the reversal of amino acid sequence, and the incorporation of D-amino acids, peptides are created in this manner maintain the placement of side chain residues, thereby preserving the structure/function relationship while bestowing protease resistance as a consequence of reversal of the peptide bonds. Using the example of BMAP-28 the consequences of retroinversion with respect to protease sensitivity, formation of conserved higher-order structure and maintenance of biological activity was examined. Importantly BMAP-28 is a multifunctional molecule that exerts both direct antimicrobial as well as immunomodulatory activity.

As anticipated, the RI-version of BMAP-28 was resistant to the action of proteases. As the therapeutic application of HDPs is currently limited by their biological lability, and subsequent required dose quantities and frequencies, this represents a methodology, provided biological activities are maintained, to reduce the costs of these treatments. The costs of D amino acids are highly comparable to L isomers and the chemistry for peptide synthesis is identical.

With respect to maintenance of biological activity the present study indicates that RI-BMAP-28 maintains or improves all of its activities. As a direct antimicrobial agent the RI-BMAP-28 was 2-3 fold more potent than its natural isomer against a spectrum of bacteria likely reflects the increased stability of the peptide rather than representing a novel mechanism of antimicrobial attack. The improvement of direct antimicrobial activity is not unexpected as the mechanism of direct antimicrobial activity is not anticipated to be dependent upon stereospecific interactions.

In contrast the ability for HDPs to modulate host immune responses likely results from interactions with either host cell proteins, receptors or otherwise. These interactions would be expected to be much more sensitive to structural and stereospecific alterations. The receptor-bound and therefore bioactive conformation of a peptide ligand can not correspond to its lowest energy non-bound conformation but can emanate from sparsely populated or non-bound conformations due to induced fit imparted by the receptor upon binding. Small peptides, unlike proteins, exist in a multiplicity of transient conformation states in dynamic equilibrium, Scherf et al., *Biochemistry* 31: 6884-6897, 1992. It has been demonstrated that HDPs tend to adopt random structures in solution and only adopt regular structural motifs upon encountering the hydrophobic environment of the membrane. Similarly associations with receptors can solidify the HDPs into active signaling structures. This appears to be the case for RI-BMAP-28 as demonstrated by its ability to induce identical cellular responses as the natural peptide with respect to the ability to suppress both patterns of gene expression as well as release of key inflammatory cytokines in LPS-stimulated cells.

An unanticipated outcome of the RI-modification is that the considerable hemolytic activity of BMAP-28 towards host cells was eliminated as a consequence of the modification. As host cell membrane disruption is believed to proceed through a similar mechanism as for the antimicrobial activity against bacterial membranes it is difficult to asses how the RI-BMAP-28 is more effective in disrupt bacterial membranes but less so against host membranes. There are two possibilities under consideration.

Firstly, one can consider whether the toxicity of the peptide is due to a degradation product rather than the full-length peptide. As the RI-BMAP-28 is largely resistant to proteolytic degradation perhaps the inability of this molecule to form a particular degradation intermediate reduces cytotoxicity. It has been demonstrated by others that the toxicity of BMAP-28 is primarily localized to a hydrophobic C-terminal tail region. As these peptides are rich in lysine and arginine residues it would be anticipated that proteolytic degradation would be mediated primarily by trypsin. Digestion of BMAP-28 with trypsin reduces the molecule to very small fragments, less than four amino acids in length, with the exception of the C-terminal hydrophobic tail where a 10 residue proteolytic fragment is generated.

Alternatively one can consider whether the differential consequences of retroinversion to the ability of the peptide to disrupt either bacterial or host membranes can reflect unique mechanisms of action that are uniquely influenced by retroinversion. The specific mechanism by which peptides disrupt membranes has not been determined but a number of unique models have been proposed. Within these models there are differential requirements for peptides to interact with each other in the context of the membrane to form higher-order structures that achieve membrane disruption. There is experimental evidence to support the occurrence of all of these models suggesting each can have a physiological role in certain circumstances. Perhaps if the disruption of host cell membranes proceeds through a mechanism which requires peptides to interact with each other in a manner that is highly dependent upon the main-chain hydrogen-bonding pattern this could account for the unique toxicities of the two peptides.

Parallels can be drawn between the application of HDPs for the manipulation of innate immune responses and that of the therapeutic agonists of Toll-like receptor 9. The ligand for this innate immune receptor is unmethylated CpG motifs that are present within bacterial DNA but largely absent from the host cell genetic material. These stimulating elements can be effectively mimicked by short strands of nucleic acids termed oligiodeoxynucleotides (ODNs) (59). As therapeutics, these molecules have considerable advantage for there cost, stability and ease of production. However the rapid pace at which CpG ODNs have progressed into clinical trials has been primarily dependent upon the ability to stabilize these molecules and thereby enhance their biological activity. In the case of the ODNs, this was achieved through a phosphothioate modification whereby one of the non-bridging oxygens was replaced with sulfur to bestow nuclease resistance. These PTO-ODNs have emerged as the standard for both investigative and clinical applications of TLR9 agonists, Klinman et al., *Nature Reviews* 4: 1-10, 2004. If retroinversion approaches emerge as a similar generic strategy to improve the therapeutic potential of host defense peptides, in particular through reduction in cytotoxicity, this modification could have similar impact on the potential of this class of therapeutics.

Example 11

Material and Methods

Bovine Model of HDP Activity.

Our selection of a bovine HDP was not without consideration. While the cow can not seem an obvious choice for an animal model, accumulating evidence suggests that the immune responses in large animal models more accurately reflect human responses than small animal models such as the mouse, Hein et al., *Nat. Rev. Immunol.* 3: 79-84, 2003. Cattle and humans share 72% sequence homology and higher sequence similarity on average than is observed between humans and mice, Jiang et al., *Genome* 45: 769-776, 2002.

While previous investigations have demonstrated the ability for HDPs to afford protection in animal species other than that from which the HDP originated this protection can result from species-independent direct antimicrobial activity rather than induced innate immune responses. That HDPs from different species have been shown to induce unique and specific patterns of gene expression in their host cells suggests that the mechanism of these peptides involved activation of specific, but overlapping, branches of innate immunity, Mookherjee et al., *J. Leokocyte. Biol.* 80:1-12, 2006. In order to permit an HDP the full opportunity to influence host cell responses it can be important to investigate peptides in animal models/cells of a common species origin. As such the ability for the peptides to modulate cellular responses in bovine cells has been examined.

Peptide Synthesis.

For this investigation two peptides were chemically synthesized, BMAP-28 ($NH_2$-GLRSLGRKILRAWKKYGPI-IVPIIRIG-COOH), and RI-BMAP-28 (D-amino acids of $NH_2$-GIRIIPVIIPGYKKWARLIKRGLSRLG-COOH).
Importantly RI-BMAP-28 was produced entirely from D-amino acids. Peptides were chemically synthesized on a Pioneer solid-phase peptide synthesizer (PerSeptive Biosystems, Foster City, Calif.) using Fmoc (9-fluorenylmethoxy carbonyl) chemistry. The peptide chains were synthesized from the carboxyl terminus to the amino terminus onto [5-(4-Fmoc-aminomethyl-3,5-dimethyloxyphenoxy)valeric acid]-polyethylene glycol-polystyrene (PAL-PEG-PS) resin. Both Fmoc-protecting groups at the amino terminus were deprotected with piperidine. The peptides were cleaved from the resin with concurrent deprotection of the side chain-protecting groups by treating the resin-bound peptide with trifluoroacetic acid (TFA) (9.3 parts) in the presence of scavengers (anisole-ethyl-methyl sulfide-1,2-ethanedithiol[3:3:1]), for 7 hours. The crude peptides were filtered from the resin, and the TFA was evaporated. Diethyl ether was added to the residues to precipitate the crude peptide. The peptides were isolated and purified by high-performance liquid chromatography (HPLC) on Vydac protein C4 columns (1.0 by 25 cm) eluting with a linear gradient of 35% buffer A ($H_2O$-0.1% TFA)-90% buffer B (acetonitrile-$H_2O$ [90/10]-0.01% TFA) for 40 mM at a flow rate of 3 ml/minute. The purity and molecular weight of the respective peptides were confirmed by matrix-assisted laser desorption ionization (MALDI)-time of flight mass spectrometry on a PE Biosystems Voyager system 4068 (National Research Council, Plant Biotechnology Institute, Saskatoon, Canada) and by amino acid analysis.

Bacterial Strains.

The bacterial strains used for this investigation were *Salmonella typhimurium* ATCC 14028, *Escherichia coli* O157:H7, *Serratia marcescens* ATCC 274, *Yersinia enterocolitica* O:9 E40 (pYV40), *Pseudomonas cepacia* ATCC 53795, and *Salmonella enterititidis* 27655R PT4.

Proteolytic Digests.

Both the natural BMAP-28 and RI-BMAP-28 (1 mg/mL) were digested with trypsin (0.1 mg/ml) in a 50 µL reaction volume (50 mM Tris pH 7.2) at 37° C. for a series of time points. Digestion mixtures were then separated via HPLC chromatography and the extent of peptide degradation quantified through comparison of peak areas to that of an undigested sample of the same peptide. High-performance liquid chromatography (HPLC) was performed on Vydac protein C4 columns (1.0 by 25 cm) eluting with a linear gradient of 35% buffer A ($H_2O$-0.1% TFA)-90% buffer B (acetonitrile-$H_2O$ [90/10]-0.01% TFA) for 30 mM at a flow rate of 1 ml/minute.

Circular Dichroism.

The mean residue molar ellipticities of peptides were determined by CD spectroscopy, using a Jasco J-720 spectropolarimeter (Jasco, Easton, Md.), at 5° C. under non-denaturing conditions (50 mM $KH_2PO_4$/$K_2HPO_4$ pH 7.0, 100 mM KCl), as well as in the presence of an α-helix inducing solvent, 2,2,2-trifluoroethanol (TFE) (50 mM $KH_2PO_4$/$K_2HPO_4$ pH 7.0, 100 mMKCl, 50% TFE). Peptides were diluted 10-fold from a 500 µM stock solution and loaded into a 0.02-cm fused silica cell. Ellipticity was determined by scanning from 190 to 250 nm. Deconvolution of the CD spectra data was carried out using the program CD Spectra Deconvolution Version 2.1©.

Determination of Minimal Inhibitory Concentration (MIC).

The MIC of the peptides were measured using a modified broth microdilution method, Wu et al., *Antimicrob. Agents Chemother.* 43: 1274-1276, 1999, in LB medium, whereby the assay was performed in sterile 96-well, round-bottom polypropylene microtitre plates with an inoculum of 5×10⁵ bacteria per mL. The plates were incubated at 37° C. for 12 h, solutions spotted onto LB-agar plates and the MIC was taken as the concentration at which no growth was observed. Each MIC assay was performed in triplicate from three different bacterial growths, the MICs reported represent the averages of these results.

PhoPQ Reporter Assays.

S. typhimurium strain CS 120, which expresses a PhoP-regulated fusion between Salmonella acid phosphatase (PhoN) and E. coli alkaline phosphatase (PhoA) was utilized for analysis of PhoPQ activation. The activity of this fusion protein was measured in salt-free LB media containing varying concentrations of the peptides and/or magnesium. For growth under PhoPQ activating conditions the growth media was supplemented with 50 µM MgCl2. Growth under PhoPQ-repressive conditions was performed in the presence of 5 mM MgCl2 as were all of the assays of peptide responses. The assay conditions utilized are based on previously described protocols, Brickman et al., *J. Mol. Biol.* 96: 307-316, 1975.

Isolation of Bovine Peripheral Blood Mononuclear Cells (PBMCs).

From each of three adult male and female cows fifty mL of blood was collected by the venupuncture method at the animal care center at the Vaccine and Infectious Disease Organization. Blood was transferred to 50 mL propylene tubes and centrifuged at 1400×g for 20 minutes at 20° C. White blood cells were isolated from the buffy coat and mixed with phosphate-buffered saline (PBSA) to a final volume of 35 mL. The cell suspension was then layered onto 15 mL of 54% isotonic Percoll (Amersham Biosciences, GH healthcare) and centrifuged at 2000×g for 20 minutes at 20° C. Cells from the Percoll-PBSA interface were then collected and washed three times with cold PBSA. Isolated PBMCs were cultured in 15 mL propylene tubes using Aim V medium (Gibco™, Invitrogen Corp., San Diego, Calif.) supplemented with 10% heat-inactivated fetal bovine serum (Gibco™).

Capture ELISAs.

Untreated cells or cells treated with LPS for 24 h, in the presence or absence of the HDPs, were centrifuged at 1000×g for 5 min followed by 10,000×g for 10 min to obtain cell-free tissue culture supernatant samples. The supernatants were subsequently aliquoted and stored at −20° C. until further use. TNF-α secretion was monitored with a species-specific capture ELISA (37). All assays were performed in triplicate. The concentration of the cytokine was quantified by establishing a standard curve with serial dilutions of the recombinant human TNF-α (eBioscience, San Diego, Calif.) or bovine TNFα (Genetech Inc. San Francisco, Calif.).

Isolation of Bovine Blood Monocytes.

Monocytes were purified from isolated PBMCs by MACS® purification using CD14 microbeads (Miltenyi Biotec Inc., Auburn, Calif.). Monocytes were then plated at $5 \times 10^6$ cells/well in 6-well plates using Aim V medium (Gibco™, Invitrogen Corp., San Diego, Calif.) supplemented with 10% heat-inactivated fetal bovine serum (Gibco™) and rested for 19 hours before stimulation.

Cell Stimulation.

The ability of BMAP-28 and RI-BMAP-28 to modulate patterns of gene expression induced by endotoxin stimulation was determined in cultured monocytes. Cultured monocytes were stimulated with purified LPS (100 ng/ml) in the presence or absence of different concentrations of antimicrobial peptides for 4 hours. Previous investigations of gene expression of cytokines and chemokines have suggested that maximal cellular responses to LPS occurred at four hours post-stimulation both in vitro, Mookherjee et al., *J. Leokocyte. Biol.* 80:1-12, 2006; Mookherjee et al., *J. Immunol.* 176: 2455-2464, 2006, and in vivo, Clapp et al., *Am. J. Respir. Cri. Care Med.* 150: 611-617, 1994. Cells were pelleted and stored at −81° C.

Total RNA Isolation.

RNA was extracted from the bovine PBMCs with the RNeasy Mini Kit (Qiagen Inc., Ontario, Canada) and the RNase-free DNase (Qiagen Inc.) as per the manufacturer's protocols.

Quantitive Real-Time PCR.

Quantitive real-time PCR (qRT-PCR) was performed using Invitrogen's SuperScript™ III Platinum® two step qRT-PCR kit with SYBR® Green (Invitrogen Corp., San Diego, Calif.) on the Bio-Rad (Hercules, Calif.) iCycler. Briefly, 250 ng total RNA, 8 µL 2×RT reaction mix, 2 µL RT enzyme, and DNase/RNase free water were added to a final volume of 20 µL. The mixture was incubated at 25° C. for 5 minutes, followed by 1 hour incubation at 50° C. and a final incubation of 15 min at 70° C. to produce the cDNA. The PCR reaction was carried out as per the manufacturer's instructions (Invitrogen Corp.) using a mix of Platinum® SYBR® Green qRT-PCR Super-Mix UDG, the template cDNA, 10 mM of the primer mix, and DNase/RNase free water up to 15 µL total volume per well. Cycling conditions were carried out as indicated by the Invitrogen's SuperScript™ III Platinum® two-step qRT-PCR kit with SYBR® Green.

Cytotoxicity Assays.

Cytotoxicity assays were performed as based upon previously established protocols, Chen et al., *Chem. Biol. Drug Des.* 67: 162-173, 2006. Briefly, peptide samples were added to 1% bovine erythrocytes in phosphate-buffered saline and reactions were incubated at 37° C. for 18 h in microtiter plates. Appropriate dilutions of the peptides were made fresh prior to each MHC trial in HDP dilution buffer (0.2% BSA, 0.01% acetic acid) and added following addition of the erythrocytes in the appropriate microtiter plate well position. Hemolysis was determined by withdrawing aliquots from the assays, removing unlysed erythrocytes by centrifugation (800×g) and determining which peptide concentrations cause hemoglobin release. Hemoglobin release was determined spectrophotometrically at 570 nm. A sample of 1% erythrocytes with no added peptide served as a non-lysis control. As erythrocytes were incubated in an isotonic medium, no detectable release (<1% of that released upon complete hemolysis) of hemoglobin was observed from this control. Similarly incubation of erythrocytes with the peptide dilution buffer did not result in detectable cell lysis.

Each recited range includes all combinations and sub-combinations of ranges, as well as specific numerals contained therein.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. An isolated modified host defense peptide that is 27 amino acids in length and at least 90% identity identical to SEQ ID NO:2.

2. A method for modulating an immune response in a vertebrate subject in need thereof comprising,
administering the modified host defense peptide of claim 1 in an amount effective to activate the immune response in the vertebrate subject.

3. The method of claim 2 wherein the modified host defense peptide consists of an amino acid sequence of SEQ ID NO:2.

4. The method of claim 1, wherein the modified host defense peptide is optionally modified, said modification selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of $CH_3CO$, $CH_3(CH_2)_nCO$, $C_6H_5CH_2CO$ and $H_2N(CH_2)_nCO$, wherein n=1-10.

5. The method of claim 2, wherein the modified host defense peptide is optionally modified as a fusion protein or a polypeptide conjugated to carbohydrate or lipid.

6. The method of claim 2, wherein the vertebrate subject is mammalian, avian, reptilian, amphibian, osteichthyes, or chondrichthyes.

7. The method of claim 2 wherein the modified host defense peptide decreases cytotoxicity to host cells in the mammalian subject compared to cytotoxicity of a naturally-occurring host defense peptide.

8. The method of claim 2 wherein the modified host defense peptide stimulates an immune response against an infectious disease in the mammalian subject.

9. The method of claim 2 wherein the modified host defense peptide has an adjuvant activity to stimulate an immune response against an infectious disease in the mammalian subject.

10. The method according to claim 9, wherein the infectious disease is a bacterial infectious disease.

11. The method of claim 10 wherein the bacterial infectious disease is a Gram-negative bacterial disease or a Gram positive bacterial disease.

12. The method according to claim 10, wherein the bacterial infectious disease is an antibiotic resistant bacterial infectious disease.

13. The method according to claim 9, wherein the infectious disease is a viral disease.

14. The method according to claim 9, wherein the infectious disease is a fungal disease.

15. The method according to claim 9, wherein the infectious disease is a parasitic disease.

16. A method for modulating an immune response in a vertebrate subject in need thereof comprising,
administering the modified host defense peptide of claim 1 in an amount effective to inhibit the immune response and reduce host cell toxicity in the vertebrate subject.

17. The method of claim 16 wherein the vertebrate subject is mammalian, avian, reptilian, amphibian, osteichthyes, or chondrichthyes.

18. The method of claim 16 wherein the modified host defense peptide decreases cytotoxicity to host cells in the mammalian subject compared to cytotoxicity of the host defense peptide.

19. The method of claim 16 wherein the modified host defense peptide reduces endotoxin activity in the vertebrate subject.

20. The method of claim 19 wherein the modified host defense peptide reduces inflammatory disease or sepsis in the vertebrate subject.

21. The method of claim 20 wherein the inflammatory disease is caused by arthritis, rheumatoid arthritis, osteoarthritis, spondylitis, gout, vasculitis, Crohn's disease, irritable bowel syndrome.

22. The method of claim 20 wherein the inflammatory disease is associated with acute or chronic pain.

23. The modified host defense peptide of claim 1, wherein the peptide consists of the amino acid sequence of SEQ ID NO:2.

24. The modified host defense peptide of claim 1 wherein the peptide is optionally modified, said modification selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of $CH_3CO$, $CH_3(CH_2)_nCO$, $C_6H_5CH_2CO$, $NH_2$, and $H_2N(CH_2)_nCO$, wherein n=1-10.

25. The modified host defense peptide of claim 1 wherein the peptide is optionally modified as a fusion protein or a polypeptide conjugated to carbohydrate or lipid.

26. A composition comprising the modified host defense peptide of claim 1, and a pharmaceutically acceptable carrier.

27. A composition comprising the modified host defense peptide of claim 23, and a pharmaceutically acceptable carrier.

28. The modified host defense peptide of claim 1, wherein the peptide is at least 95% identical to SEQ ID NO:2.

* * * * *

SEQUENCE LISTING

<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Arg Ser Leu Gly Arg Lys Ile Leu Arg Ala Trp Lys Lys Tyr
1               5                   10                  15

Gly Pro Ile Ile Val Pro Ile Ile Arg Ile Gly
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Gly
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Ile
<220> FEATURE:
<221> NAME/KEY: MOD_RES
<222> LOCATION: (5)..(5)
<223> OTHER INFORMATION: D-Ile
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Val
<220> FEATURE:
<221> NAME/KEY: MOD_RES
<222> LOCATION: (8)..(8)
<223> OTHER INFORMATION: D-Ile
<220> FEATURE:
<221> NAME/KEY: MOD_RES
<222> LOCATION: (9)..(9)
<223> OTHER INFORMATION: D-Ile
<220> FEATURE:
<221> NAME/KEY: MOD_RES
<222> LOCATION: (10)..(10)
<223> OTHER INFORMATION: D-Pro
<220> FEATURE:
<221> NAME/KEY: MOD_RES
<222> LOCATION: (11)..(11)
<223> OTHER INFORMATION: D-Gly
<220> FEATURE:
<221> NAME/KEY: MOD_RES
<222> LOCATION: (12)..(12)
<223> OTHER INFORMATION: D-Tyr
<220> FEATURE:
<221> NAME/KEY: MOD_RES
<222> LOCATION: (13)..(13)
<223> OTHER INFORMATION: D-Lys

```
<220> FEATURE:
<221> NAME/KEY: MOD_RES
<222> LOCATION: (14)..(14)
<223> OTHER INFORMATION: D-Lys
<220> FEATURE:
<221> NAME/KEY: MOD_RES
<222> LOCATION: (15)..(15)
<223> OTHER INFORMATION: D-Trp
<220> FEATURE:
<221> NAME/KEY: MOD_RES
<222> LOCATION: (16)..(16)
<223> OTHER INFORMATION: D-Ala
<220> FEATURE:
<221> NAME/KEY: MOD_RES
<222> LOCATION: (17)..(17)
<223> OTHER INFORMATION: D-Arg
<220> FEATURE:
<221> NAME/KEY: MOD_RES
<222> LOCATION: (18)..(18)
<223> OTHER INFORMATION: D-Leu
<220> FEATURE:
<221> NAME/KEY: MOD_RES
<222> LOCATION: (19)..(19)
<223> OTHER INFORMATION: D-Ile
<220> FEATURE:
<221> NAME/KEY: MOD_RES
<222> LOCATION: (20)..(20)
<223> OTHER INFORMATION: D-Lys
<220> FEATURE:
<221> NAME/KEY: MOD_RES
<222> LOCATION: (21)..(21)
<223> OTHER INFORMATION: D-Arg
<220> FEATURE:
<221> NAME/KEY: MOD_RES
<222> LOCATION: (22)..(22)
<223> OTHER INFORMATION: D-Gly
<220> FEATURE:
<221> NAME/KEY: MOD_RES
<222> LOCATION: (23)..(23)
<223> OTHER INFORMATION: D-Leu
<220> FEATURE:
<221> NAME/KEY: MOD_RES
<222> LOCATION: (24)..(24)
<223> OTHER INFORMATION: D-Ser
<220> FEATURE:
<221> NAME/KEY: MOD_RES
<222> LOCATION: (25)..(25)
<223> OTHER INFORMATION: D-Arg
<220> FEATURE:
<221> NAME/KEY: MOD_RES
<222> LOCATION: (26)..(26)
<223> OTHER INFORMATION: D-Leu
<220> FEATURE:
<221> NAME/KEY: MOD_RES
<222> LOCATION: (27)..(27)
<223> OTHER INFORMATION: D-Gly

<400> SEQUENCE: 2

Gly Ile Arg Ile Ile Pro Val Ile Pro Gly Tyr Lys Lys Trp Ala
1               5                   10                  15

Arg Leu Ile Lys Arg Gly Leu Ser Arg Leu Gly
            20                  25

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ser Arg Ile Val Pro Ala Ile Pro Val Ser Leu Leu
1               5                   10
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5
```